(12) United States Patent
Fedorchak et al.

(10) Patent No.: US 12,396,959 B2
(45) Date of Patent: Aug. 26, 2025

(54) THERMORESPONSIVE HYDROGEL CONTAINING POLYMER MICROPARTICLES FOR NONINVASIVE OCULAR DRUG DELIVERY

(71) Applicant: University of Pittsburgh—Of the Commonwealth System of Higher Education, Pittsburgh, PA (US)

(72) Inventors: Morgan V. Fedorchak, Wexford, PA (US); Steven R. Little, Allison Park, PA (US); Joel S. Schuman, Pittsburgh, PA (US); Anthony Cugini, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 5 days.

(21) Appl. No.: 17/580,988

(22) Filed: Jan. 21, 2022

(65) Prior Publication Data

US 2022/0211632 A1 Jul. 7, 2022

Related U.S. Application Data

(62) Division of application No. 14/772,758, filed as application No. PCT/US2014/020355 on Mar. 4, 2014, now Pat. No. 11,246,838.

(Continued)

(51) Int. Cl.
*A61K 9/00* (2006.01)
*A61K 9/06* (2006.01)
(Continued)

(52) U.S. Cl.
CPC .......... *A61K 9/5021* (2013.01); *A61K 9/0048* (2013.01); *A61K 9/0051* (2013.01);
(Continued)

(58) Field of Classification Search
CPC ..................................... A61K 9/5021
See application file for complete search history.

(56) References Cited

U.S. PATENT DOCUMENTS

| 5,837,226 A | 11/1998 | Jungherr et al. |
| 6,264,971 B1 | 7/2001 | Darougar et al. |

(Continued)

FOREIGN PATENT DOCUMENTS

| WO | WO 2011/106702 | 9/2011 |
| WO | WO 2012/044952 | 4/2012 |

(Continued)

OTHER PUBLICATIONS

Park, An Anti-angiogenic Reverse Thermal Gel as a Drug-Delivery System for Age-Related Wet Macular Degeneration, Macromolecular Bioscience, 2013, 13, 464-469 (Year: 2013).*

(Continued)

*Primary Examiner* — Paul W Dickinson
(74) *Attorney, Agent, or Firm* — Fish & Richardson P.C.

(57) ABSTRACT

A method for sustained delivery of an agent to an ocular organ in a subject, comprising topically delivering to the ocular surface a liquid thermoresponsive hydrogel comprising agent-loaded polymer microparticles, wherein the agent is sustainably released for a period of at least five days.

21 Claims, 9 Drawing Sheets

Related U.S. Application Data

(60) Provisional application No. 61/773,076, filed on Mar. 5, 2013.

(51) Int. Cl.
*A61K 9/10* (2006.01)
*A61K 9/50* (2006.01)
*A61K 31/498* (2006.01)
*A61K 47/34* (2017.01)

(52) U.S. Cl.
CPC .................. *A61K 9/06* (2013.01); *A61K 9/10* (2013.01); *A61K 9/5031* (2013.01); *A61K 31/498* (2013.01); *A61K 47/34* (2013.01)

(56) References Cited

U.S. PATENT DOCUMENTS

| | | |
|---|---|---|
| 6,656,460 B2 | 12/2003 | Benita et al. |
| 7,060,299 B2 | 6/2006 | Alavattam et al. |
| 7,589,057 B2 | 9/2009 | Chang et al. |
| 8,298,569 B2 | 10/2012 | Philips et al. |
| 8,492,334 B2 | 7/2013 | Lavik et al. |
| 8,980,248 B2 | 3/2015 | Shoichet et al. |
| 9,018,006 B2 | 4/2015 | Stepkowski et al. |
| 9,056,045 B2 | 6/2015 | Hughes et al. |
| 9,655,862 B2 | 5/2017 | Mousa |
| 9,757,276 B2 | 9/2017 | Penhasi |
| 9,937,256 B2 | 4/2018 | Knipe et al. |
| 9,937,278 B2 | 4/2018 | Steinberg et al. |
| 10,376,592 B2 | 8/2019 | Acharya et al. |
| 10,624,865 B2 | 4/2020 | Pathak |
| 11,246,838 B2 | 2/2022 | Fedorchak et al. |
| 2001/0049369 A1 | 12/2001 | Jablonski et al. |
| 2002/0197300 A1 | 12/2002 | Schultz et al. |
| 2006/0018911 A1 | 1/2006 | Ault-Riche et al. |
| 2006/0173060 A1 | 8/2006 | Chang et al. |
| 2006/0235084 A1 | 10/2006 | Heller et al. |
| 2006/0246145 A1 | 11/2006 | Chang et al. |
| 2009/0252781 A1 | 10/2009 | Sawhney et al. |
| 2010/0209478 A1 | 8/2010 | Sawhney et al. |
| 2010/0261646 A1 | 10/2010 | Lavik et al. |
| 2011/0189291 A1 | 8/2011 | Yang et al. |
| 2011/0206773 A1 | 8/2011 | Lavik et al. |
| 2012/0040397 A1 | 2/2012 | Luo et al. |
| 2012/0148676 A1 | 6/2012 | Little |
| 2012/0156176 A1 | 6/2012 | Fujimoto et al. |
| 2012/0231072 A1 | 9/2012 | Kang-Mieler et al. |
| 2013/0189230 A1 | 7/2013 | Shoichet et al. |
| 2014/0086975 A1 | 3/2014 | Sinko et al. |
| 2014/0086995 A1 | 3/2014 | Ratner et al. |
| 2014/0271863 A1 | 9/2014 | Anderson et al. |
| 2014/0343413 A1 | 11/2014 | Jolck et al. |
| 2014/0343476 A1 | 11/2014 | Penhasi |
| 2015/0037422 A1 | 2/2015 | Kaplan et al. |
| 2015/0087671 A1 | 3/2015 | McClain et al. |
| 2015/0140106 A1 | 5/2015 | Mousa |
| 2015/0374633 A1 | 12/2015 | Fedorchak et al. |
| 2016/0058698 A1 | 3/2016 | Mayadunne et al. |
| 2016/0166504 A1 | 6/2016 | Jarrett et al. |
| 2016/0206741 A1 | 7/2016 | Knipe et al. |
| 2017/0189546 A1 | 7/2017 | Bidwell, III et al. |
| 2017/0348254 A1 | 12/2017 | O'Neil |
| 2019/0046479 A1 | 2/2019 | Pathak |
| 2019/0099365 A1 | 4/2019 | Fedorchak et al. |
| 2020/0246179 A1 | 8/2020 | Peyman |
| 2020/0360282 A1 | 11/2020 | Fedorchak et al. |
| 2021/0369649 A1 | 12/2021 | Fedorchak et al. |
| 2022/0202705 A1 | 6/2022 | Fedorchak et al. |

FOREIGN PATENT DOCUMENTS

| | | |
|---|---|---|
| WO | WO 2012/169972 | 12/2012 |
| WO | WO 2014/074823 | 5/2014 |
| WO | WO 2014/138085 | 9/2014 |
| WO | WO 2015/001087 | 1/2015 |
| WO | WO 2017/165449 | 9/2017 |
| WO | WO 2018/206749 | 11/2018 |

OTHER PUBLICATIONS

Aburahma et al., "Biodegradable ocular inserts for sustained delivery of brimonidine tartarate: preparation and in vitro/in vivo evaluation," AAPS PharmSciTech, Dec. 2011, 12(4):1335-1347.

Babiuch, retrieved from the retinal physician website: www.retinalphysician.com/issues/2017/june-2017/ new-monoclonal-antibody-treatments-in-retina on Aug. 19, 2019, 4 pages.

Bald et al., "2-Chloro-1-Methylquinolinium Tetrafluoroborate as an Effective and Thiol Specific UV-Tagging Reagent for Liquid Chromatography," J. Liq. Chromatogr. Relat. Technologies, 2001, 24(9):1323-1339.

Berge et al., "Pharmaceutical salts," J. Pharm. Sci., 66(1):1-19, Jan. 1977.

Chang et al., "Biodegradable PLGA-based Drug Delivery Systems for Modulating Ocular Surface Disease under Experimental Murine Dry Eye," J. Clin. Exp. Ophthalmol., 2(11): 13 pages, Nov. 1, 2011.

Chen et al., "Selection and analysis of an optimized anti-VEGF antibody: crystal structure of an affinity-matured Fab in complex with antigen," J. Mol. Bio., 293(4):865-81, Nov. 1999.

Cui et al., "New Hydrolysis-Dependent Thermosensitive Polymer for an Injectable Degradable System," Biomacromolecules, 8(4):1280-1286, Apr. 2007.

Derwent and Mieler, "Thermoresponsive hydrogels as a new ocular drug delivery platform to the posterior segment of the eye," Transactions of the American Ophthalmological Society, 106:206-214, Dec. 2008.

Doiron et al., "Preparation and initial characterization of biodegradable particles containing gadolinium-DTPA contrast agent for enhanced MRI," Proc. Nat. Acad. Sci. USA, Nov. 11, 2008, 105(45):17232-17237.

Extended European Search Report issued for European Application No. 14761105.7 on Jul. 22, 2016.

Fedorchak et al., "28-day intraocular pressure reduction with a single dose of brimonidine tartrate-loaded microspheres," Experimental Eye Research, vol. 125, 210-216, Jun. 28, 2014.

Fedorchak et al., "28-Day Ocular Delivery of Brimonidine Tartrate from Rationally Designed Degradable Microparticles in a Rabbit Model," presentation delivered at AIChE annual meeting Oct. 31, 2012.

Fedorchak et al., "28-Day Ocular Delivery of Brimonidine Tartrate from Rationally Designed Degradable Microparticles in a Rabbit Model," presentation delivered at Society for Biomaterials Oct. 4, 2012.

Fedorchak et al., "Advanced Controlled Release Systems for Next Generation Ophthalmic Therapy," presentation delivered at Gordon Research Conference Mar. 22, 2012.

Fedorchak et al., "Combating Blindness with Convenient and Comfortable Glaucoma Treatments," presentation delivered at ARVO annual meeting May 4, 2012.

Fedorchak et al., "Combating Blindness with Convenient and Comfortable Glaucoma Treatments," presentation delivered at McGowan Institute for Regenerative Medicine annual retreat Mar. 5, 2012.

Friedman et al., "Prevalence of open-angle glaucoma among adults in the United States," Arch. Ophthalmol., Apr. 2004, 122(4):532-538.

Fujimoto et al., "Synthesis, Characterization and Therapeutic Efficacy of a Biodegradable, Thermoresponsive Hydrogel Designed for Application in Chronic Infarcted Myocardium," Biomaterials, 30(26):4357-4368, Sep. 2009.

Gao et al., "A Microparticle/Hydrogel Combination Drug-Delivery System for Sustained Release of Retinoids," Investigative Ophthalmology & Visual Science, 53:10, 6314-6323, Sep. 2012.

Ghate et al., "Barriers to Glaucoma Drug Delivery," J. Glaucoma, Mar. 2008, 17(2):147-156.

Gu et al., "Controlled release of recombinant human nerve growth factor (rhNGF) from poly [(lactic acid)-co-(glycolic acid)]microspheres

(56) References Cited

OTHER PUBLICATIONS for the treatment of neurodegenerative disorders," Polymer International, 56( 10): 1272-1280, Oct. 2007.
Guan et al., "Protein-reactive, Thermoresponsive Copolymers With High Flexibility and Biodegradability," Biomacromolecules, 9(4):1283-92, Apr. 2008.
Hermann et al., "Electronic compliance monitoring of topical treatment after ophthalmic surgery," Int. Ophthalmol., Apr. 7, 2010, 30:385-390.
Hu et al., "Controlled Release Bevacizumab in Thermoresponsive Hydrogel Found to Inhibit Angiogenesis," Biomed. Mater. Eng., 24:1941-50, 2014.
Ibrahim et al., "Novel Topical Ophthalmic Formulations for Management of Glaucoma," Pharmaceutical Research, 30(11): 2818-2831, Nov. 15, 2013.
International Search Report issued in PCT/US2014/020355 mailed Jul. 10, 2014, 5 pages.
Jimenez et al., "A sustained release cysteamine microsphere/thermoresponsive gel eyedrop for corneal cystinosis improves drug stability," Drug Deliv. Transl. Research, Feb. 4, 2021, 11(5):2224-2238.
Karamanos et al., "Development of an HPLC method for determining the alpha2-adrenergic receptor agonist brimonidine in blood serum and aqueous humor of the eye," Biomed. Chromatogr., 1999, 13:86-88.
Knight et al., "Sustained drug delivery in glaucoma," Current Opinion in Ophthamology, 25(2): 112-117, Mar. 2014.
Kusmierek et al., "Measurement of reduced and total mercaptamine in urine using liquid chromatography with ultraviolet detection," Biomed. Chromatography, Jan. 18, 2008, 22(4):441-445.
Lambiase et al., "Experimental and clinical evidence of neuroprotection by nerve growth factor eye drops: Implications for glaucoma," PNAS, 106(32): 13469-13474, Aug. 11, 2009.
Lee and Vernon, "In Situ-Gelling, Erodible N-isopropylacrylamide Copolymers," Macromol. Biosci., 5(7):629-635, Jul. 2005.
MacCallum et al., "Antibody-antigen Interactions: Contact Analysis and Binding Site Topography," J. Mol. Biol., 262(5):732-45, Oct. 1996.
Na et al., Langmuir 2010; 26:11165-11169.
Nanjawade et al., "In situ-forming hydrogels for sustained ophthalmic drug delivery," J. Control Release., 122(2):119-34, Sep. 2007.
Nussenblatt et al. Retina, 2013; 30:1579-1587. doi:10.1097/IAE.0b013e3181e7878e.
Pascual-Camps et al. J. Ophthal. Inflam. Infect. 2014; 4:26. www.joii-journal.conn/content/4/1/26.
Pescina et al., "Effect of pH and penetration enhancers on cysteamine stability and trans-corneal transport," Eur. J. Pharm. Biopharmaceutics, Oct. 2016, 107: 171-179.
Rudikoff et al., "Single amino acid substitution altering antigen-binding specificity," Proc. Natl. Acad. Sci. U.S.A., 79(6):1979-1983, Mar. 1982.
Sánchez et al., "Development of biodegradable microspheres and nanospheres for the controlled release of cyclosporin A," Int. J. Pharmaceutics, Oct. 15, 1993, 99(2-3):263-273.
Shanbhag et al., "Macrophage/particle interactions: effect of size, composition and surface area," J. Biomed. Mater. Res., Jan. 1994, 28(1):81-90.
Turturro et al., "The effects of cross-linked thermo-responsive PNIPAAm-based hydrogel injection on retinal function," Biomaterials, 32(14):3620-6, May 2011.
Wang et al., "Novel Thermosensitive Hydrogel Injection Inhibits Post-Infarct Ventricle Remodelling," Eur. J. Heart Fail, 11(1):14-19, Jan. 2009.
Wang et al., "Synthesis, Characterization and Surface Modification of Low Moduli Poly(ether Carbonate Urethane)ureas for Soft Tissue Engineering," Acta. Biomater., 5(8):2901-12, Oct. 2009.
Wang et al., "The nerve growth factor signaling and its potential as therapeutic target for glaucoma," BioMed Research International, Aug. 31, 2014.
Wikipedia.org [online], "Cysteamine," dated Sep. 7, 2018, retrieved from URL<https://en.wikipedia.org/w/index.php?title=Cysteamine&oldid=858431558>, 5 pages.
Wikipedia.org [online], "Freeze drying," dated Nov. 6, 2018, retrieved from URL<https://en.wikipedia.org/w/index.php?title=Freeze-drying&oldid=924871987>, 12 pages.
Wu et al., "Humanization of a murine monoclonal antibody by simultaneous optimization of framework and CDR residues," J. Mol. Biol., 294(1):151-162, Nov. 1999.
Wu et al., "Toward the development of partially biodegradable and injectable thermoresponsive hydrogels for potential biomedical applications," ACS Appl. Mater. Interf., 1(2):312-327, Feb. 2009.
Xu et al. Macromolecules, 2007; 40:9103-9110.
Yang et al., "Hybrid Dendrimer Hydrogel/PLGA Nanoparticle Platform Sustains Drug Delivery for One Week and Antiglaucoma Effects for Four Days Following One-Time Topical Administration," ACS Nano, 6(9): 7595-7606, Aug. 9, 2012.
Zhang and Zhuo, "Synthesis and in vitro drug release behavior of amphiphilic triblock copolymer nanoparticles based on poly (ethylene glycol) and polycaprolactone," Biomaterials, 26(33):6736-42, Nov. 2005.
Zhang et al., "Absolute quantification of poly(dl-lactide-co-glycolide) in microspheres using quantitative 1H NMR spectroscopy," J. Pharm. Biomed. Analysis, Nov. 30, 2017, 146:273-278.
Zweers et al., "Release of anti-restenosis drugs from poly(ethylene oxide)-poly(dl-lactic-co-glycolic acid) nanoparticles," J. Control. Release, Sep. 12, 2006, 114(3):317-324.
U.S. Appl. No. 17/281,647, filed Mar. 31, 2021, Morgan Virginia Fedorchak, Published as U.S. Patent Application Publication No. 2021/0369649.
U.S. Appl. No. 17/577,816, filed Jan. 18, 2022, Morgan Virginia Fedorchak, Pending.
Shams et al., "Treatment of corneal cystine crystal accumulation in patients with cystinosis," Clin. Ophthalmol, Oct. 2014, 8:2077-2084.
Bhagav et al., "Sustained release ocular inserts of brimonidine tartrate for better treatment in open-angle glaucoma," Drug Deliv. Transl. Res., Apr. 2011, 1(2):161-174.
Fedorchak et al., "Long Term Glaucoma Drug Delivery Using a Topically Retained Gel/Microsphere Eye Drop," Sci. Rep., Aug. 2017, 7:8639.
Luaces-Rodriguez et al., "Cysteamine polysaccharide hydrogels: Study of extended ocular delivery and biopermanence time by PET imaging," Int. J. Pharm., Aug. 2017, 528(1-2):714-722.
Wan et al., "Modulating protein release profiles by incorporating hyaluronic acid into PLGA microparticles via a spray dryer equipped with a 3-fluid nozzle," Pharm. Res., Nov. 2014, 31(11):2940-2951.
Maren et al., "Ocular pharmacology of methazolamide analogs: distribution in the eye and effects on pressure after topical application," J. Pharmacol. Exp. Ther., Apr. 1987, 241(1):56-63.

* cited by examiner

FIG. 4A
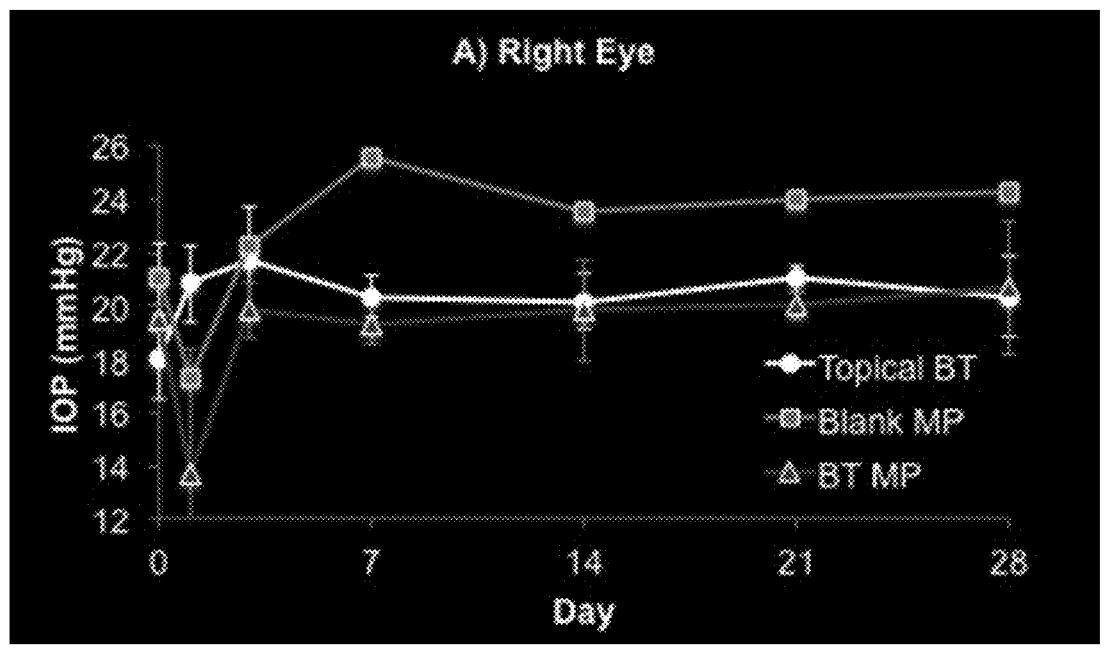
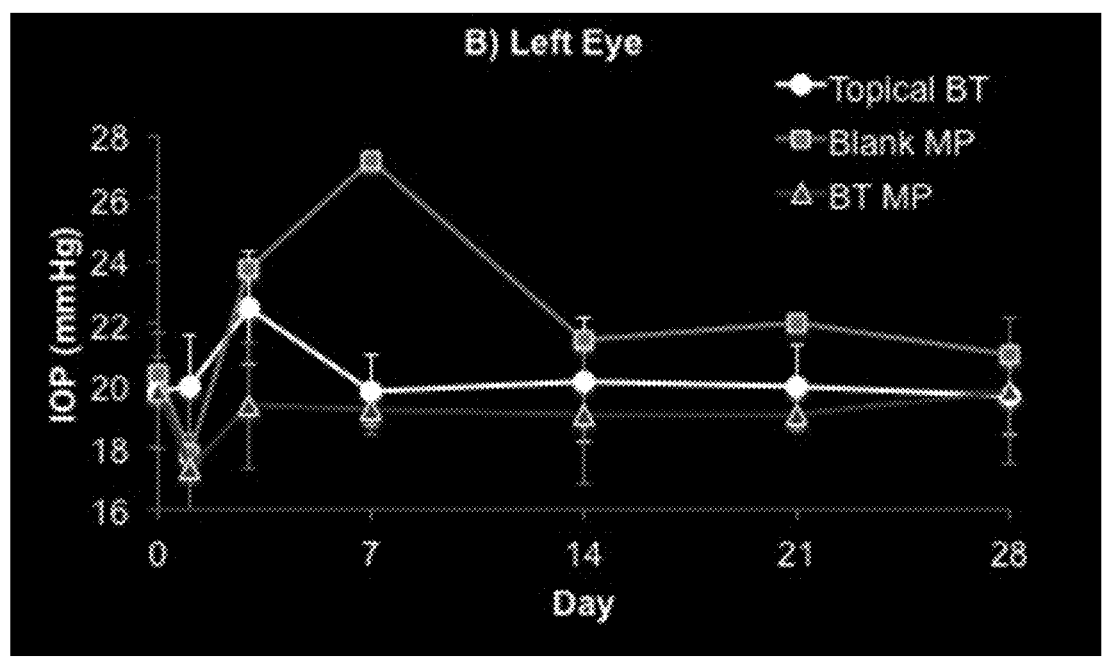
FIG. 4B

FIG. 5A
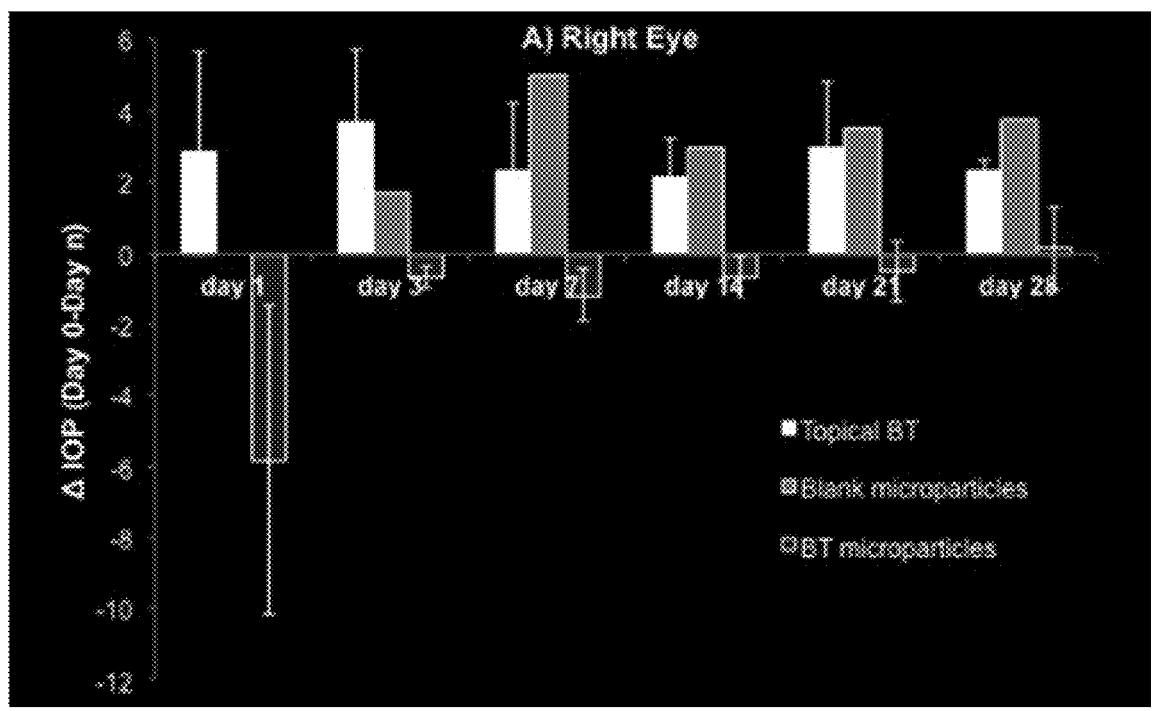
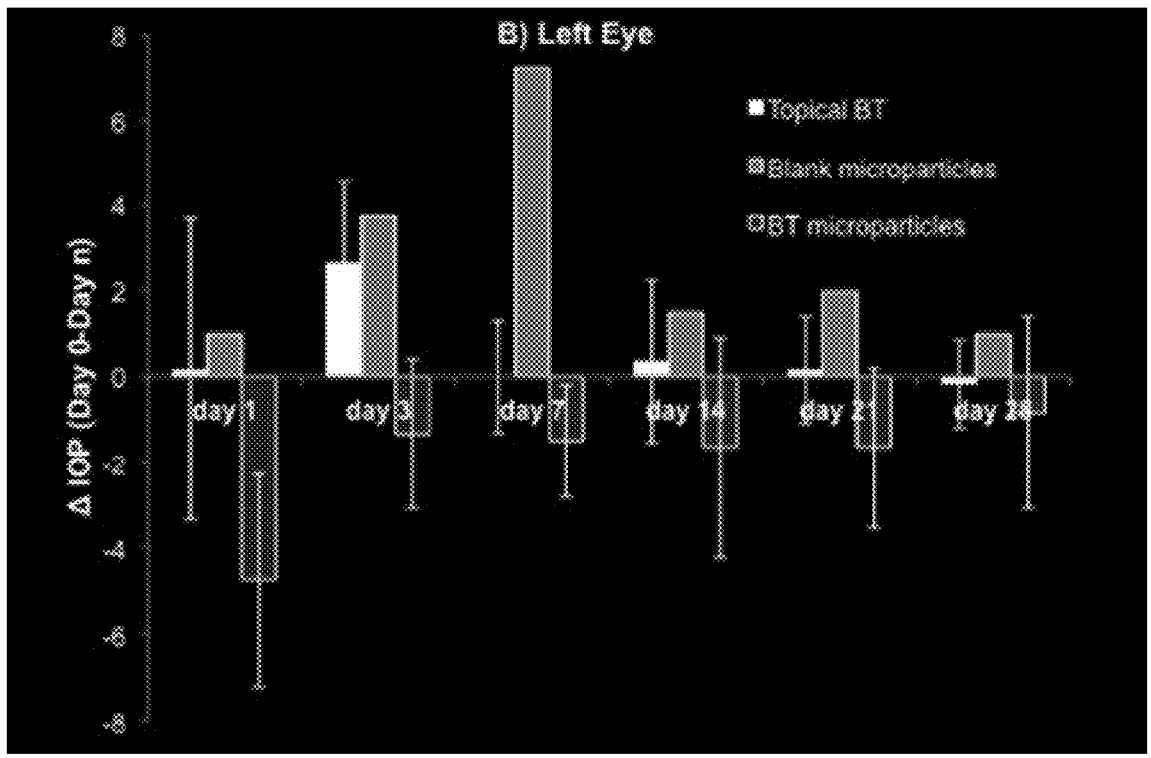
FIG. 5B

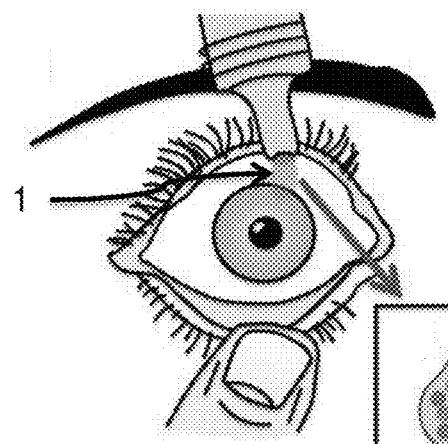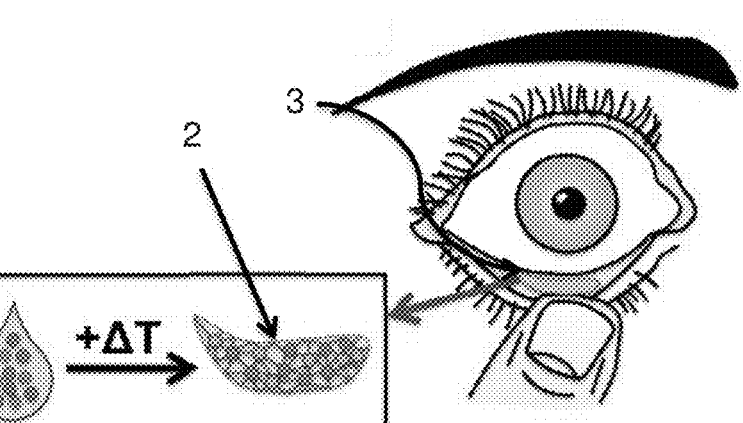
FIG. 7A
FIG. 7B
FIG. 7C
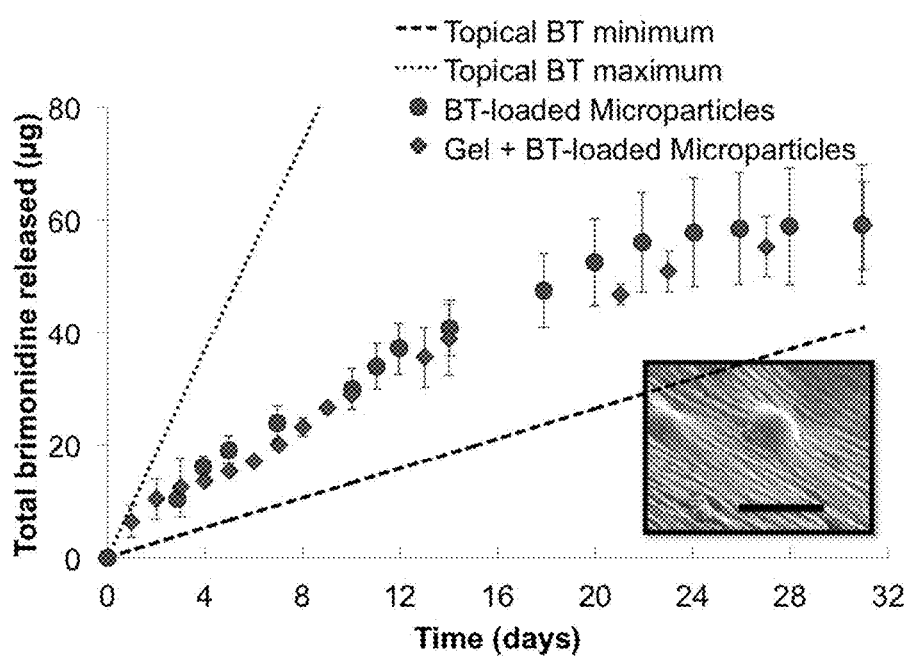
FIG. 8

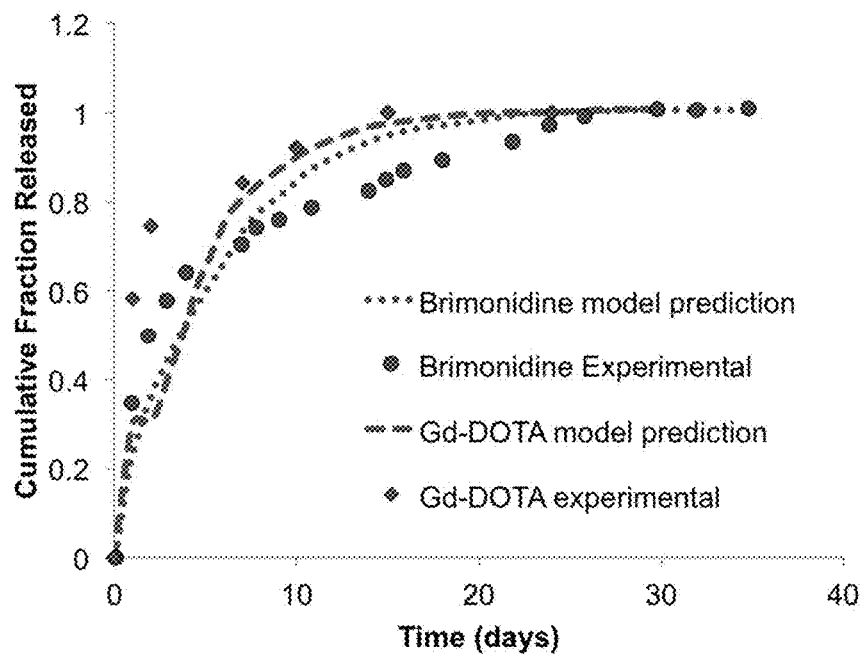
FIG. 9
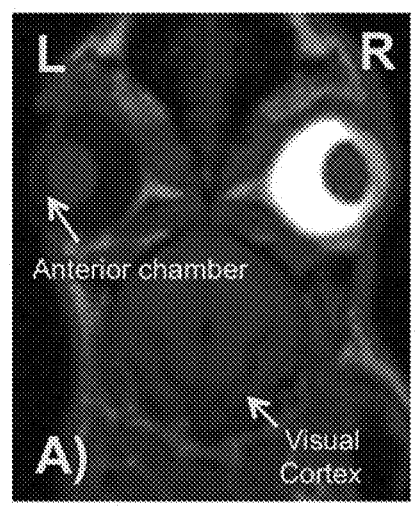
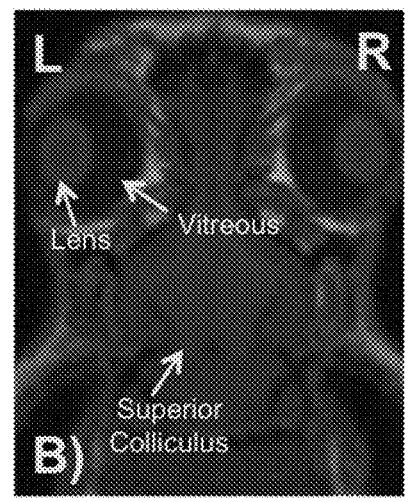
FIG. 10A    FIG. 10B

Day 7  Day 14  Day 21  Day 28

FIG. 14A
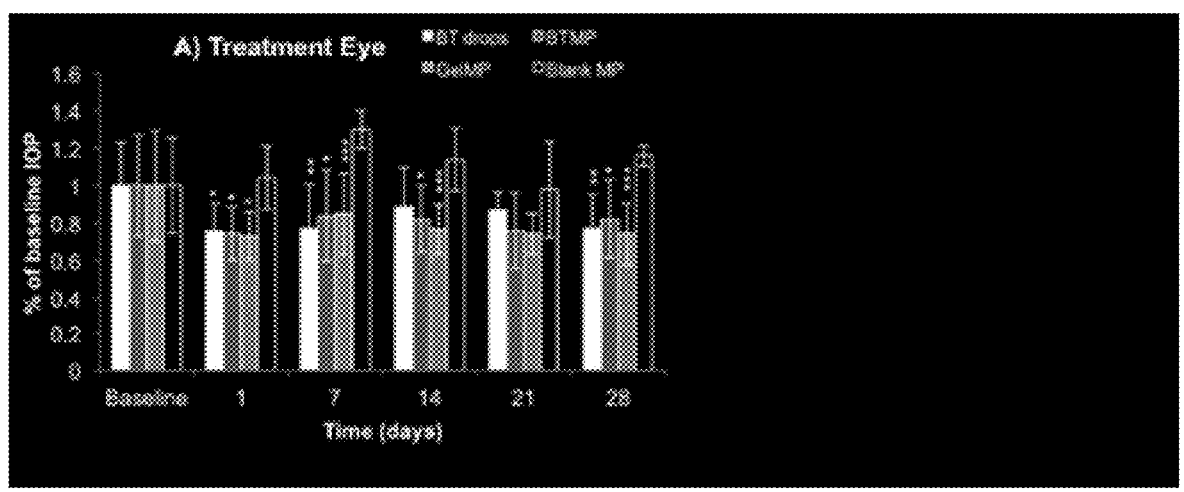
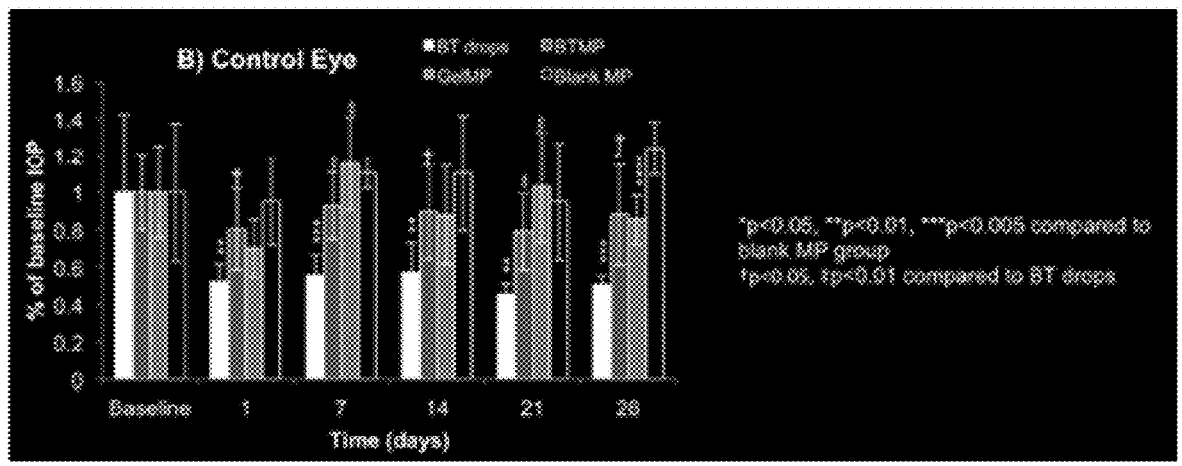
FIG. 14B

THERMORESPONSIVE HYDROGEL CONTAINING POLYMER MICROPARTICLES FOR NONINVASIVE OCULAR DRUG DELIVERY

PRIORITY CLAIM

This application is a divisional of U.S. patent application Ser. No. 14/772,758, filed Sep. 3, 2015, which is a § 371 National Phase of PCT Application No. PCT/US2014/020355, filed Mar. 4, 2014, which claims priority to and the benefit of U.S. Patent Application No. 61/773,076, filed Mar. 5, 2013, all of which are incorporated by reference in their entirety.

BACKGROUND

It is estimated that nearly 4 million adults will be diagnosed with open angle glaucoma by the year 2020, the majority of which will be treated with a daily regimen of ocular hypotensive medication (Friedman et al., 2004). These IOP-reducing drugs are given as eye drops, which must be administered frequently by the patient to reduce the risk of irreversible vision loss. The rigorous dosing schedule, initial lack of symptoms, and difficult drop administration lead to extremely low patient compliance rates (Hermann et al., 2010). Additionally, eye drop administration requires high concentrations of drug to overcome the many absorption barriers in the eye (Ghate and Edelhauser, 2008).

One of the main risk factors for glaucoma, the second leading cause of blindness worldwide, is sustained ocular hypertension. Intraocular pressure (IOP) reduction in glaucoma patients is typically accomplished through the administration of eye drops several times daily, the difficult and frequent nature of which contributes to compliance rates as low as 50%. Brimonidine tartrate (BT), a common glaucoma medication which requires dosing every 8-12 hours, has yet to be adapted into a controlled-release formulation that could drastically improve compliance.

SUMMARY

One embodiment disclosed herein is a method for sustained delivery of an agent to an ocular organ in a subject, comprising topically delivering to the ocular surface a liquid thermoresponsive hydrogel comprising agent-loaded polymer microparticles, wherein the agent is sustainably released for a period of at least five days.

A further embodiment disclosed herein is a method for ocular delivery of an agent comprising administering the agent at the lower fornix of an eye in a subject, wherein the method comprises topically delivering to an eye a liquid hydrogel comprising agent-loaded polymer microparticles, and permitting the liquid hydrogel to form in situ a gelled, sustained release structure residing in the lower fornix of the eye.

Also disclosed herein is a composition comprising agent-loaded polymer microparticles dispersed within a thermoresponsive hydrogel, wherein the agent is an agent for treating an ocular condition and the composition is configured for sustained topical ocular release of the agent.

Additionally disclosed herein is a drug depot positioned in the lower fornix of an eye of a subject, wherein the drug depot comprises a gelled hydrogel comprising drug-loaded polymer microparticles.

The foregoing will become more apparent from the following detailed description, which proceeds with reference to the accompanying figures.

BRIEF DESCRIPTION OF THE DRAWINGS

FIGS. 4A and 4B: Actual IOP measurements in each of the three groups taken from FIG. 4A) the right eye (treated eye) and FIG. 4B) the left eye (untreated eye). N=3 for BTMP and topical BT groups; n=2 for blank MP group.

FIGS. 5A and 5B: Delta IOP values (baseline minus current day) for each of the three groups in FIG. 5A) the right eye (treated eye) and FIG. 5B) the left eye (untreated eye). N=3 for BTMP and topical BT groups; n=2 for blank MP group.

FIGS. 7A, 7B and 7C: A representation of an embodiment for administering an embodiment of the microparticle/hydrogel delivery system disclosed herein.

FIG. 8: Agent release is not affected when microparticles are loaded into hydrogel. Inset: SEM of hydrogel containing BT-loaded microparticles (scale bar=10 µm).

FIG. 9: Theoretical and actual release of Gd-DOTA and brimonidine from polymer microparticles (brimonidine release data from FIGS. 2 and 8 with y-axis modified to represent % of total release).

FIGS. 10A and 10B: Whole brain T1-weighted MR images of NZW at 24 h after intravitreal injection of thermoresponsive gel containing FIG. 10A) Gd-DOTA-loaded MPs and FIG. 10B) soluble Gd-DOTA only. Injections were in the right eye only; scans performed within 1 h of sacrifice.

FIGS. 14A and 14B: Intraocular pressure data for BT drops (positive control), BT-loaded microparticles (BTMP, prior experimental treatment), gel/BTMP (GelMP, current experimental treatment), and blank microparticles (blank MP, negative control). These results were reported for the treated eye (FIG. 14A) and the untreated contralateral eye (FIG. 14B). The legend indicating statistic significance applies to both FIG. 14A and FIG. 14B.

DETAILED DESCRIPTION

Terminology

Figure 1:
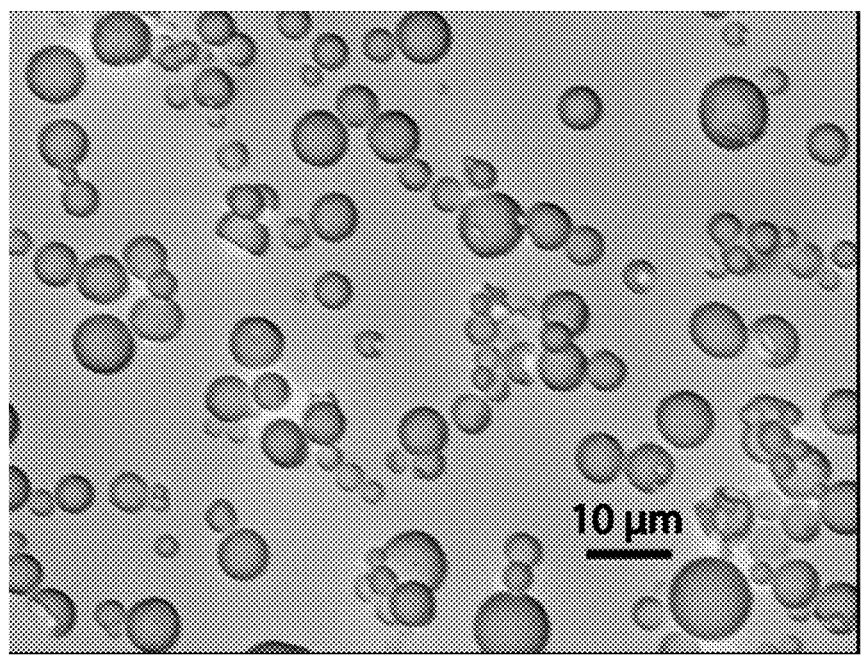
FIG. 1: SEM images of brimonidine tartrate-loaded PLGA microparticles (BTMPs). These images confirm the desired size and morphology of the BTMPs, consistent with volume impedance measurements (average volume diameter=7.46±2.86 µm).

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of a an agent disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the microparticles disclosed herein.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range; the term is used in reference to particles of sizes that can be, for example, administered to the eye in the form of an eye drop that can be delivered from a squeeze nozzle container, and thus can be less than 50 nm to 100 microns or greater. In certain embodiments, microparticles specifically refers to particles having a diameter from about 1 to about 25 microns, preferably from about 10 to about 25 microns, more preferably from about 10 to about 20 microns. In one embodiment, the particles have a diameter from about 1 to about 10 microns, preferably from about 1 to about 5 microns, more preferably from about 2 to about 5 microns. As used herein, the microparticle encompasses microspheres, microcapsules and microparticles, unless specified otherwise. A microparticle may be of composite construction and is not necessarily a pure substance; it may be spherical or any other shape.

"Ocular region" or "ocular site" means any area of the eye, including the anterior and posterior segment of the eye, and which generally includes, but is not limited to, any functional (e.g., for vision) or structural tissues found in the eyeball, or tissues or cellular layers that partly or completely line the interior or exterior of the eyeball. Ocular regions include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat an ocular condition, or reduce or prevent ocular injury or damage without causing significant negative or adverse side effects to the eye or a region of the eye "Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as glaucoma. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments, "treating" means reduction or resolution or prevention of an ocular condition, ocular injury or damage, or to promote healing of injured or damaged ocular tissue "Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, PA (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include C1-C22 fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Delivery Systems

Disclosed herein are microparticle/hydrogel ocular delivery systems. The delivery systems disclosed herein are noninvasive since a microparticle/hydrogel suspension can be self-administered to the lower fornix and removed by the subject (e.g., with tweezers or a saline solution). Current applications for microparticles or hydrogels for ocular conditions require injection to the anterior chamber or vitreous by a clinician. In addition, the current clinical standard is topical eye drop medication that lasts a few hours. In contrast, the presently disclosed systems could provide sustained delivery for at least one month.

The agent for inclusion in the delivery systems disclosed may be a therapeutic agent, a diagnostic agent, an imaging agent, a cosmetic agent, or other agents. In one embodiment, the one or more therapeutic agents are useful for treating ocular conditions. Suitable classes of therapeutic agents include, but are not limited to, active agents that lower intraocular pressure, antibiotics (including antibacterials and anitfungals), anti-inflammatory agents, chemotherapeutic agents, agents that promote nerve regeneration, steroids, immunosuppressants, neuroprotectants, dry eye syndrome treatment agents (e.g., immunosuppressants, anti-inflammatory agents, steroids, comfort agent such as carboxymethyl cellulose), and combinations thereof. The therapeutic agents described above can be administered alone or in combination to treat ocular conditions.

In one embodiment, the microparticles contain one or more active agents that manage (e.g., reduce) elevated IOP in the eye. Suitable active agents include, but are not limited to, prostaglandins analogs, such as travoprost, bimatoprost, latanoprost, unoprostine, and combinations thereof; and carbonic anhydrase inhibitors (CAL), such as methazolamide, and 5-acylimino- and related imino-substituted analogs of methazolamide; and combinations thereof. The microparticles can be administered alone or in combination with microparticles containing a second drug that lowers IOP.

In a further embodiment, the agent may be a beta adrenergic receptor antagonist or an alpha adrenergic receptor agonist.

Illustrative beta adrenergic receptor antagonists include timolol, levobunalol, carteolol, metipranolol, betaxolol, or a pharmaceutically acceptable salt thereof, or combinations thereof. Illustrative alpha adrenergic receptor agonists include brimonidine, apraclonidine, or a pharmaceutically acceptable salt thereof, or combinations thereof. Additional examples of anti-glaucoma agents include pilocarpine, epinephrine, dipivefrin, carbachol, acetazolamide, dorzolamide, brinzolamide, latanoprost, and bimatoprost.

The agent may be an antibiotic. Illustrative antibiotics include, but are not limited to, cephaloridine, cefamandole, cefamandole nafate, cefazolin, cefoxitin, cephacetrile sodium, cephalexin, cephaloglycin, cephalosporin C, cephalothin, cafcillin, cephamycins, cephapirin sodium, cephradine, penicillin BT, penicillin N, penicillin O, phenethicillin potassium, pivampic ulin, amoxicillin, ampicillin, cefatoxin, cefotaxime, moxalactam, cefoperazone, cefsulodin, ceflizoxime, ceforanide, cefiaxone, ceftazidime, thienamycin, N-formimidoyl thienamycin, clavulanic acid, penemcarboxylic acid, piperacillin, sulbactam, cyclosporine, moxifloxacin, vancomycin, and combinations thereof.

The agent may be an inhibitor of a growth factor receptor. Suitable inhibitors include, but are not limited to, inhibitors of Epidermal Growth Factor Receptor (EGFR), such as AG1478, and EGFR kinase inhibitors, such as BIBW 2992, erlotinib, gefitinib, lapatinib, and vandetanib.

The agent may be a chemotherapeutic agent and/or a steroid. In one embodiment, the chemotherapeutic agent is methotrexate. In another embodiment, the steroid is prednisolone acetate, triamcinolone, prednisolone, hydrocortisone, hydrocortisone acetate, hydrocortisone valerate, vidarabine, fluorometholone, fluocinolone acetonide, triamcinolone acetonide, dexamethasone, dexamethasone acetate, loteprednol etabonate, prednisone, methylprednisone, betamethasone, beclometasone, fludrocortisone, deoxycorticosterone, aldosterone, and combinations thereof.

Illustrative immunosuppressants include pimecrolimus, tacrolimus, sirolimus, cyclosporine, and combinations thereof.

In certain embodiments, the amount of agent loaded into the microparticles may from 1 ng to 1 mg, more particularly 1 to 100 μg, and most particularly, 20 to 30 μg agent per mg of microparticles. In certain specific embodiments, the amount of agent loaded into the microparticles is 25 30 μg agent per mg of microparticles.

The polymers for the microparticle may be bioerodible polymers so long as they are biocompatible. Preferred bio-erodible polymers are polyhydroxyacids such as polylactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpryrrolidone, alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

The preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, referred to as 502H); poly(D,L-lactic-co-glycolic acid) (PLGA, 50:50 lactic acid to glycolic acid ratio, $M_n$=25 kDa, referred to as 503H); poly(D,L-lactic-co-glycolic acid) (PLGA, 50:50 lactic acid to glycolic acid ratio, $M_n$=30 kDa, referred to as 504H); poly(D,L-lactic-co-glycolic acid) (PLGA, 50:50 lactic acid to glycolic acid ratio, $M_n$=35 kDa, referred to as 504); and poly(D,L-lactic-co-glycolic acid) (PLGA, 75:25 lactic acid to glycolic acid ratio, $M_n$=10 kDa, referred to as 752).

In certain embodiments, the polymer microparticles are biodegradable.

The agent-loaded microparticles may have a volume average diameter of 200 nm to 30 μm, more particularly 1 to 10 μm. In certain embodiments, the agent-loaded microparticles do not have a volume average diameter of 10 μm or greater since such larger particles are difficult to eject from a container in the form of an eye drop. The agent-loaded microparticles may be pore less or they may contain varying amounts of pores of varying sizes, typically controlled by adding NaCl during the synthesis process.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics.

In certain embodiments, the hydrogel may respond to external stimulus (e.g., physiological conditions) such as changes in ion concentration, pH, temperature, glucose, shear stress, or a combination thereof. Illustrative hydrogels include polyacrylamide (e.g., poly-N-isopropylacrylamide), silicon hydrogels like those used in contact lenses, polyethylene oxide/polypropylene oxide or combinations of the two (e.g., Pluronics hydrogel or Tectronics hydrogel), butyl methacrylate, polyethylene glycol diacrylate, polyethylene glycol of varying molecular weights, polyacrylic acid, poly methacrylic acid, poly lactic acid, poly(tetramethyleneether glycol), poly(N,N'-diethylaminoethyl methacrylate), methyl methacrylate, and N,N'-dimethylaminoethylmethacrylate. In certain embodiments, the hydrogel is a thermoresponsive hydrogel.

In certain embodiments, the thermoresponsive hydrogel has a lower critical solution temperature (LCST) below body temperature. The thermoresponsive hydrogel remains fluid below physiological temperature (e.g., 37° C. for humans) or at or below room temperature (e.g., 25° C.), solidify (into a hydrogel) at physiological temperature, and are biocompatible. For example, the thermoresponsive hydrogel may be a clear liquid at a temperature below 34° C. which reversibly solidifies into a gelled composition at a temperature above 34° C. Generally, the LCST-based phase transition occurs upon warming in situ as a result of entropically-driven dehydration of polymer components, leading to polymer collapse. Various naturally derived and synthetic polymers exhibiting this behavior may be utilized. Natural polymers include elastin-like peptides and polysaccharides derivatives, while notable synthetic polymers include those based on poly(n-isopropyl acrylamide) (PNIPAAm), poly(N,N-dimethylacrylamide-co-N-phenylacrylamide), poly(glycidylmethacrylate-co-N-isopropylacrylamide), poly(ethylene oxide)-b-poly(propylene oxide)-b-poly(ethylene oxide), poly(ethylene glycol)-polyester copolymer, and amphiphilic block copolymers. The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to about 2 upon the hydrophobic collapse above the LCST (32-34° C.). In certain embodiments, the amphiphilic block copolymer comprises a hydrophilic component selected from poly ethylene oxide (PEO), poly vinyl alcohol (PVA), poly glycolic acid (PGA), poly (N-isopropylacrylamide), poly(acrylic acid) (PAA), poly vinyl pyrrolidone (PVP) or mixtures thereof, and a hydrophobic component selected from polypropylene oxide (PPO), poly (lactic acid) (PLA), poly (lactic acid co glycolic acid) (PLGA), poly (.beta.-benzoyl L-aspartate) (PBLA), poly (.gamma.-benzyl-L-glutamate) (PBLG), poly (aspartic acid), poly (L-lysine), poly(spermine), poly (caprolactone) or mixtures thereof. Examples of such amphiphilic block copolymers include (PEO)(PPO)(PEO) block copolymers (PEO/PPO), and poly (lactic acid co glycolic acid) block copolymers (PLGA), such as (PEO)(PLGA)(PEO) block copolymers.

In certain embodiments, the hydrogel is non-biodegradable (e.g., PNIPAAm). In other embodiments, the hydrogel is biodegradable. For example, biodegradable NIPAAm-based polymers can be made by conjugating the PNIPAAm with natural biodegradable segments such as MMP-susceptible peptide, gelatin, collagen, hyaluronic acid and dextran. Copolymers formed from NIPAAm and monomers with degradable side chains comprise another category of NIPAAm-based bioabsorbable, thermoresponsive hydrogels. Hydrolytic removal of hydrophobic side chains increases the hydrophilicity of the copolymer, raising the LCST above body temperature and making the polymer backbone soluble. Due to the relative simplicity of the synthetic process, the most investigated biodegradable monomers have been HEMA-based monomers, such as 2-hydroxyethyl methacrylate-polylactide (HEMA-PLA) (Lee, B. H.; et al. Macromol. Biosci. 2005, 5, 629-635; and Guan, J., et al. Biomacromolecules 2008, 9, 1283-92), 2-hydroxyethyl methacrylate-polycaprolactone (HEMA-PCL) (Wang, T., et al. Eur. J. Heart Fail 2009, 11, 14-19 and Wu, D., et al. ACS Appl. Mater. Interf. 2009, 2, 312-327) and 2-hydroxyethyl methacrylate-polytrimethylene carbonate (HEMA-PTMC) (Fujimoto, K. L., et al. Biomaterials 2009, 30, 4357-4368 and Wang, F., et al. Acta Biomater. 2009, 5, 2901). However, the backbone remnant following hydrolysis, HEMA, presents hydroxyethyl side groups (—$CH_2CH_2$-OH), which have a relatively limited effect on remnant polymer hydrophilicity (Cui, Z., et al. Biomacromolecules 2007, 8, 1280-1286). In previous studies, such hydrogels have been found to be either partially bioabsorbable (Wu, D., et al. ACS Appl. Mater. Interf. 2009, 2, 312-327) or completely bioabsorbable, but have required the inclusion of considerably hydrophilic co-monomers such as acrylic acid (AAc) in the hydrogel synthesis (Fujimoto, K. L.; et al. Biomaterials 2009, 30, 4357-4368; Wang, F., et al. Acta Biomater. 2009, 5, 2901; and Guan, J., et al. Biomacromolecules 2008, 9, 1283-92).

In a further embodiment, the thermoresponsive hydrogel degrades and dissolves at physiological conditions in a time-dependent manner. The copolymer and its degradation products typically are biocompatible. According to one embodiment, the copolymer consists essentially of N-isopropylacrylamide (NIPAAm) residues (a residue is a monomer incorporated into a polymer), hydroxyethyl methacrylate (HEMA) residues and methacrylate-polylactide (MAPLA) macromer residues as disclosed in U.S. Patent Publ. 2012/0156176, which is incorporated herein by reference. Alternately, the copolymer consists essentially of N-isopropylacrylamide residues, acrylic acid (AAc) residues, and hydroxyethyl methacrylate-poly(trimethylene carbonate) (HEMAPTMC) macromer residues as disclosed in U.S. Patent Publ. 2012/0156176, which is incorporated herein by reference.

The base precursor (e.g., a prepolymer, oligomer and/or monomer) for the hydrogel, cross linkers, and initiators are mixed together and allowed to polymerize for a predefined period of time (from 1 h to 24 h typically) to form the hydrogel. The hydrogel is then washed to remove any excess initiator or unreacted materials. The hydrogel at this stage is a liquid (e.g., in the form of an aqueous solution) at room temperature until it is ready for use. The microparticles can be added in before, after, or during the polymerization of the hydrogel (adding microparticles in before or during polymerization results in a slighter faster initial drug release rate)

to form a suspension of solid microparticles in hydrogel. The amount of microparticles loaded into the hydrogel may vary. For example, there may be up to 10 mg, more particularly 1 to 5 mg microparticles per microliter hydrogel. In certain embodiments, the microparticles are homogeneously dispersed within the hydrogel. Optional components can be added that allow for easier visualization of the hydrogel/microparticle suspension such as sodium fluorescein or other fluorescent molecules such as FITC, rhodamine, or AlexaFluors or dyes such as titanium dioxide. The water content of the swollen hydrogel at room temperature may be 50-80%. The water content of the hydrogel after it gels in situ in the eye may be 1-10%.

Upon ocular administration of the microparticle/hydrogel liquid suspension, the microparticle/hydrogel system releases water and can become an opaque solid gel member. The gelled member may be sufficiently firm that it can be manipulated with tweezers. FIG. 7A depicts administration of an eye drop 1 comprising the microparticle/hydrogel liquid suspension, gelling of the suspension to form a polymeric crosslinked matrix 2 that encapsulates the agent-loaded microparticles (FIG. 7B), and positioning of the resulting gelled member 3 in the lower fornix of the eye (FIG. 7C). In one particular embodiment, a thermoresponsive hydrogel carrier for the agent-loaded microparticles has been developed and characterized that will allow patients to apply a liquid suspension (containing the release system) topically to their eye as they would an aqueous eye drop-based medication (FIG. 7A). When the drop collects in the conjunctival cul-de-sac, the liquid warms to body temperature and thermoresponsive hydrogel de-swells, forming a stable, opaque gel (FIG. 7B). The drop also appears to naturally conform to the shape of the inferior fornix during the gelation (FIG. 7C) promoting retention of the system and continuous delivery of agent to the eye via the embedded, sustained agent microparticle formulation. The gel/microparticle system could afford sustained release of an ocular drug for up to 30 times longer than any currently known in situ forming hydrogels. Furthermore, removal of the gelled drop would be as simple as flushing the eye with cold saline, unlike intravitreal or subconjunctival implants that require removal by a clinician. This formulation should lower IOP and increase bioavailability compared to topical eye drops. This new delivery formulation could also serve as a modular platform for local administration of not only a variety of glaucoma medications (including BT), but a whole host of other ocular therapeutics as well.

The shape of the gelled member 3 may vary and is dependent on the anatomy of the ocular structure. Typically, the gelled member 3 spreads out into an elongate, thin film of gel, but it may assume a more cylindrical shape. In certain embodiments, the gelled film may have a thickness of 10 to 1000, more particularly 100 to 300 μm. The gel can be manipulated as it undergoes phase transitioning into a desired shape. In certain embodiments, the gelled member may retain pliability to a certain extent. In certain embodiments, the gelled member 3 may have a residence time in the lower fornix of at least five days, more particularly at least 10 days, and most particularly at least 30 days.

The microparticle/hydrogel system disclosed herein may provide for sustained release of an agent. The agent release can be linear or non-linear (single or multiple burst release). In certain embodiments, the agent may be released without a burst effect. For example, the sustained release may exhibit a substantially linear rate of release of the therapeutic agent in vivo over a period of at least 5 days, more particularly at least 10 days, and most particularly at least 30 days. By substantially linear rate of release it is meant that the therapeutic agent is released at a rate that does not vary by more than about 20% over the desired period of time, more usually by not more than about 10%. It may be desirable to provide a relatively constant rate of release of the agent from the delivery system over the life of the system. For example, it may be desirable for the agent to be released in amounts from 0.1 to 100 μg per day, more particularly 1 to 10 μg per day, for the life of the system. However, the release rate may change to either increase or decrease depending on the formulation of the polymer microparticle and/or hydrogel. In certain embodiments, the delivery system may release an amount of the therapeutic agent that is effective in providing a concentration of the therapeutic agent in the eye in a range from 1 ng/ml to 200 μg/ml, more particularly 1 to 5 μg/ml. The desired release rate and target drug concentration can vary depending on the particular therapeutic agent chosen for the drug delivery system, the ocular condition being treated, and the subject's health.

In certain embodiments, the agent release is dependent on degradation of the polymer microparticles. As the polymer chains break up, the agent can diffuse out of the initial polymer microparticle matrix where it will eventually reach the hydrogel matrix. At that point, the hydrogel may partially slow down release of the agent but diffusion through the hydrogel is significantly faster than degradation of the polymer. Thus the limiting factor in agent release is degradation of the polymer.

It is clearly more desirable to demonstrate a method of directly measuring the concentrations of release agents diffusing into target tissues directly in vivo for sustained delivery systems. Such a technology would help researchers ensure that enough drug is administered to the affected tissues while at the same time minimizing the risk of potential systemic side effects. Additionally, if a controlled release system were to be modified (in the future) to incorporate other modalities (such as growth factor-based neuroprotective agents or antibody-based antiangiogenics), knowledge of the amount of drug that reaches posterior tissues could significantly expedite the development of such a therapy and provide vastly more information than functional measurements (like IOP) alone. Unfortunately, available methods to detect or visualize in vivo release are currently both limited and unwieldy. For example, traditional drug detection assay methods (such as those using radiolabeled drug) require large numbers of animals for serial sacrifice-type studies to measure in vivo drug concentrations in resected tissue. Additionally, the reduced drug concentrations associated with controlled release can make it even more difficult to detect drug in the local microenvironment, let alone in surrounding tissues or systemic circulation.

Accordingly, disclosed herein are embodiments to encapsulate an MRI contrast agent, e.g., gadolinium-tetraazocyclododecanetetraacetic acid (Gd-DOTA) in the same polymer microparticles as those used to release the therapeutic agent and perform in vivo scans over the full treatment window of at least one month, thus representing the use of MRI to visualize and quantify long-term controlled release in the eye from a topical depot. Rationally-designed, long-term, polymer microparticle based delivery of Gd-based MRI contrast agents can serve as a reliable, noninvasive method to resolve the spatial and temporal release profile of a variety of therapeutic agents, beginning with BT, from the topical gel/microparticle formulation described herein. BT and Gd-DOTA have very similar molecular weights (approximately 440 and 600 Da, respectively), meaning that degradable release systems that produce practically identical release profiles for both agents can be designed. Furthermore, the ocular half-lives of Gd-DTPA (a contrast agent very similar in size and structure to Gd-DOTA) and BT are 28.08 and 28.2 min, respectively, lending further support to the use of Gd-DOTA as a surrogate imaging marker for BT. Correspondingly, the measurement of local Gd-DOTA concentrations using MRI may allow tracking of in vivo release behavior for both formulations (Gd-DOTA and BT), which can be confirmed (or validated) using the traditional, high-sensitivity BT assay detection methods. Preliminary ex vivo MRI data for Gd-DOTA-loaded microparticles suggest that these methods are feasible as a real time, noninvasive quantification method. The unique delivery system described herein would allow quantification of Gd-DOTA release from a topical depot, unlike previously mentioned studies that were performed using either implants or injections into the eye. In addition, if future release formulations are identified that would require sustained delivery of large proteins (>>600 Da Gd-DOTA), it is also now possible to conjugate Gd-DOTA onto these proteins (not significantly increasing the molecular size of the release agents) to track their release and distribution into the eye.

The microparticle/hydrogel composition may be administered in the form of a liquid eye drop. The eye drop(s) may be administered to any ocular structure, but is preferably administered to the lower fornix. The eye drops may be self-administered by the subject. The eye drop will conform comfortably to the conjunctival sac and release the loaded agent. The eye drop may be administered on a regimen wherein the interval between successive eye drops is greater than at least one day (although in certain embodiments the eye drop may be administered once daily or more than once daily). For example, there may be an interval of at least 5 days, at least one week, or at least one month between administrations of an eye drop(s). In preferred embodiments, the disclosed eye drops may be used for sustained monthly delivery of medication as a replacement for the current clinical standard of once or twice daily eye drop administration. At the end of the desired administration period, the gelled member can be removed from the eye (for example, via a tweezer or flushing out). In certain embodiments, the hydrogel may be biodegradable so that there is no need to remove the gelled member (this embodiment may be most useful for treating an acute condition). This system disclosed herein not only drastically decreases the dosing frequency (thereby increasing the likelihood of patient compliance and recovery/prevention of worsening symptoms), it does so while avoiding clinician involvement for administration by being completely noninvasive.

The microparticle/hydrogel disclosed herein may include an excipient component, such as effective amounts of buffering agents, and antioxidants to protect a drug (the therapeutic agent) from the effects of ionizing radiation during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

The microparticle/hydrogel system disclosed herein may be useful to treat a variety of ocular conditions, both chronic and acute. Illustrative ocular conditions include: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemiretinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In certain embodiments, the ocular conditions include glaucoma, chronic dry eye, keratitis, post-operative inflammation, conjunctivitis, and bacterial or fungal infections.

Also disclosed herein are methods of controlling IOP in a subject using the above-described drug delivery systems. In various embodiments, IOP is maintained at or below about 22 mmHg. The drug may be released such that the concentration of the drug is approximately constant over a period of at least one day. In other embodiments, the above methods control the IOP for a period of at least 1 day, 2 days, 3 days, or 1 week.

Examples

Formation of Drug-Loaded Microparticles
Summary

BT was encapsulated in poly(lactic-co-glycolic) acid (PLGA) microparticles using a standard double emulsion procedure. In vitro drug release from the BT-loaded microparticles was quantified using UV-Vis spectroscopy. For in vivo studies, rabbits were randomized to receive a single subconjunctival injection of blank (no drug) or BT-loaded microparticles or twice-daily topical BT 0.2% drops. IOP was monitored over 28 days along with regular slit lamp examination. Additionally, aqueous humor samples were periodically taken and analyzed for BT concentration using high-performance liquid chromatography. Following sacrifice on Day 28, eyes were enucleated and stained for histology. The drug loaded microparticles demonstrated a primarily poreless morphology with a volume average diameter of 7.5±2.9 μm. They released an average of 2.1±0.37 μg BT/mg particles/day in the in vitro setup. In vivo, the decrease in IOP was significantly lower in the treated eye for topical BT versus BT microparticles. In contrast, IOP steadily increased in rabbits injected with the blank microparticles. Additionally, BT levels in the aqueous humor were maintained below toxic levels throughout the study. No evidence of microparticle migration or foreign body response was observed in the enucleated eyes following the 28-day study. The BT-loaded PLGA microparticles deliver over 28 days of BT with a single dose, as confirmed using in vitro release assays. This represents a vast improvement over the current standard of 56-84 doses. These microparticles demonstrated effectiveness at reducing IOP in vivo, with no evidence of irritation or infection.

Materials and Methods

2.1 Microparticle (MP) Fabrication

MPs were fabricated using a standard double emulsion procedure (Sanchez et al., 1993; Zweers et al., 2006). Briefly, 200 mg of polylactic-co-glycolic) acid (MW 24-38 kDa, viscosity 0.32-0.44 dl/g; Sigma, St. Louis, MO) was mixed with 4 ml of dichloromethane (DCM) and 12.5 mg of an aqueous brimonidine tartrate solution (Santa Cruz Biotechnologies, Santa Cruz, CA). The drug/polymer solution was sonicated for 10 s (Sonics VibraCell™) before homogenization in 60 ml 2% poly(vinyl alcohol) (PVA-MW ~25,000 Da, 98% hydrolyzed, Polysciences) for 1 min at approximately 7000 RPM (Silverson L4RT-A homogenizer). This double emulsion was then added to 80 ml of 1% PVA and allowed to mix for 3 h to evaporate any remaining DCM. MPs were then washed four times by centrifuging for 5 min at 1000 RPM. The MPs were resuspended in DI water and placed in a lyophilizer (Virtis Benchtop K freeze dryer, Gardiner, NY) operating at 70 mTorr for 48 hours before being stored at −20° C.

2.2 Microparticle Characterization

The shape and morphology of the MPs was examined using a scanning electron microscope (SEM). Images were taken on the lyophilized blank and drug-loaded MPs following gold sputter-coating using a JEOL 6335F Field Emission SEM (JEOL, Peabody, MA). Average particle diameter for a minimum of 10,000 MPs was determined using volume impedance measurements on a Multisizer 3 Coulter Counter (Beckman Coulter, Indianapolis, IN).

2.3 In Vitro Release Assay

Known masses of lyophilized MPs were suspended in phosphate buffered saline (PBS) and incubated at 37° C. MP suspensions were centrifuged for 10 min at 1000 RPM after predetermined intervals of time and the supernatant was removed for analysis. Brimonidine concentration in PBS samples was measured via UV/Vis absorption using a SoftMax Pro 5 microplate reader (Molecular Devices, Sunnyvale, CA) at 320 nm. The MP aliquots were then resuspended in fresh PBS. The results for BT-loaded MPs are reported as the average of three release studies and their standard deviation. Any background signal obtained from the blank MPs was subtracted from each measurement.

Theoretical maximum and minimum amounts of BT absorption were also calculated as a basis for comparison for in vitro release from the BTMPs. This range was calculated by assuming a 50 μl drop and 2 drops administered per day at a rate of either 1% (minimum) or 7% (maximum) absorption (Ghate and Edelhauser, 2008). As the in vitro release methods measure base brimonidine and not the tartrate salt, a necessary conversion factor of 0.66 mg brimonidine for every 1 mg BT was incorporated in these calculations (Acheampong et al., 2002).

2.4 In Vivo Studies

Pigmented Dutch belted rabbits were randomized to receive either blank MPs (no drug), BTMPs, or 0.2% BT drops (Alphagan®, Allergan, Irvine, CA), with three animals in each group initially. In order to ensure that statistical significance could be achieved with the minimal number of animals (as required by IACUC), a sample size analysis was performed with a power of 0.8 based on previous results comparing IOP measurements before and after topical BT 0.2% administration and insertion of an experimental ocular insert delivery system in a rabbit model (Aburahma and Mahmoud, 2011), leading to a n=3 rabbits per group. On day 0, the right eye of rabbits in the blank or drug-loaded MP groups received a superior subconjunctival injection of 5 mg of MPs suspended in 0.050 cc sterile saline. Rabbits in the BT drops group received a single drop of 0.2% BT solution in one eye twice a day for every day of the study. The left eye remained untreated in all animals throughout the study.

Samples of venous blood and aqueous humor were taken on Days 0 (prior to administration of treatment), 1, 3, 7, 14, 21, and 28. These samples were stored at −20° C. prior until assaying for brimonidine concentration assay using high performance liquid chromatography (HPLC, see below). Eyes were regularly checked for signs of infection or irritation by instilling sodium fluorescein drops in each eye and examining with a portable slit lamp containing a cobalt blue light (Reichert Technologies, Depew, NY). IOP was also measured in both eyes using a Model 30 Classic pneumatonometer (Reichert Technologies, Depew, NY). Tonometry was always performed between the hours of 8 am and 11 am and immediately at the induction of intravenous anesthesia with a 1:10 mix of xylazine and ketamine Approximately 0.09 ml of anesthetic was required.

Animals were sacrificed on Day 28, and both treated and untreated eyes were enucleated for histological analysis. The eyes were embedded in paraffin prior to sectioning and staining with hematoxylin and eosin, periodic acid-Schiff (PAS), or Masson's trichrome stain. All slides were analyzed for any evidence of intra- or extra-ocular abnormalities by a masked examiner.

2.5 HPLC Analysis

Methods for analyzing brimonidine content in aqueous humor and plasma were adapted from those in Karamanos et al. (1999) (Karamanos et al., 1999). Samples were analyzed using an UltiMate 3000 HPLC system (Dionex, Sunnyvale, CA) to ensure that toxic levels of drug were not detectable either locally or systemically. Briefly, approximately 20 μl samples were taken for reverse-phase, isocratic HPLC analysis. A Supelcosil LC-18 column (Sigma Aldrich) was used with 10% (v/v) acetonitrile in TEA buffer as the mobile phase. The separation was performed at room temperature at a flow rate of 1.0 ml/min. Retention time was approximately 5-10 min and brimonidine was detected at a wavelength of 248 nm.

2.6 Statistical Analysis

One-way analysis of variance (ANOVA) was performed on baseline IOP measurements to ensure that the three groups could be considered samples from a single population. Subsequently, ΔIOP was calculated at each time point, defined as the group-specific change in average IOP from Day 0. ΔIOP at each time point for the BTMP group was compared to the positive control topical BT drops group using a two tailed, two-sample student's t-test with a significance criterion of 5%. This calculation requires 3 samples and therefore could not be performed against the blank MP negative control group due to an anesthesia-related complication in one animal in this group early in the study.

3. Results 3.1 Microparticles

To test the hypotheses, a controlled release system capable of 1 month of brimonidine tartrate (BT) administration was required. As described above, this anti-glaucoma medication was encapsulated in degradable PLGA microparticles (MPs) successfully using a double emulsion technique. A preliminary in vitro characterization of the MPs was performed to confirm their suitability for use in a subconjunctival injection model prior to beginning assays of drug release. Although a formulation's in vitro release behavior is not ipso facto analogous to how release would proceed in vivo, it can indeed be indicative of either local or topical release scenarios and is, regardless, an important part of the overall characterization of a new, prototype formulation.

FIG. 1 shows scanning electron microscope (SEM) images of the brimonidine tartrate-loaded MPs (BTMPs). These images confirm that a smooth surface and uniform shape were achieved according to our design specifications. These images also agree with volume impedance measurements, which determined the volume average diameter of the BTMPs to be 7.46±2.86 μm. This size distribution is as expected for the conditions used to fabricate the BTMPs. Ultimately, these MPs are small enough to be easily injected with a 30-gauge needle while still being large enough to avoid phagocytic removal or migration from the site of injection (Shanbhag et al., 1994).

Figure 2:
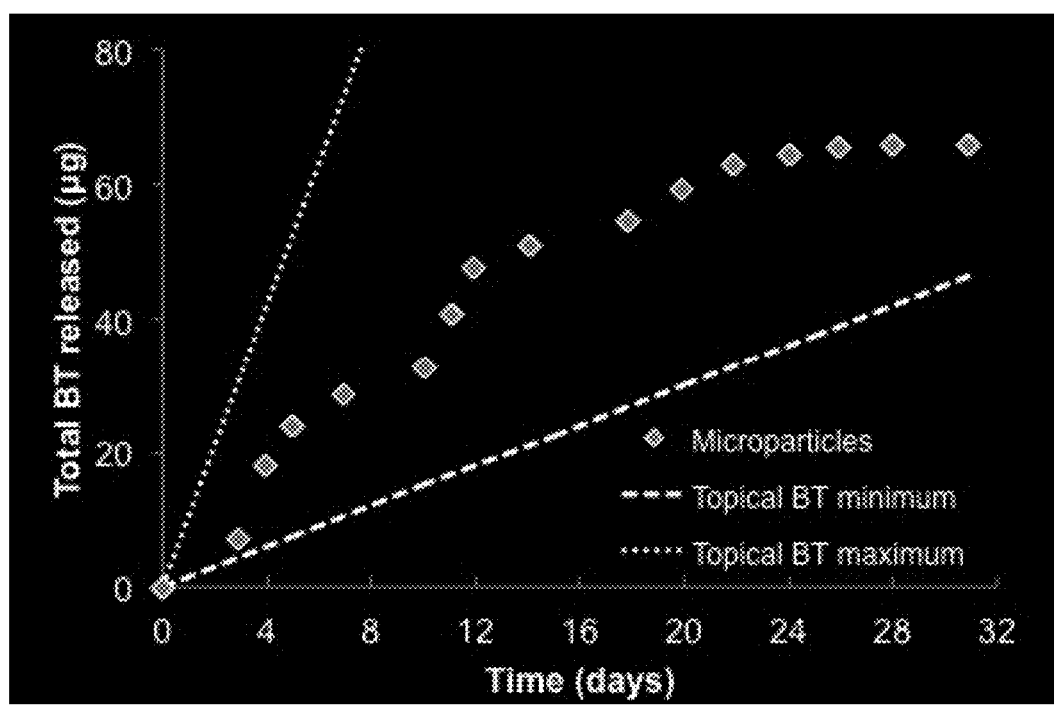
FIG. 2: In vitro release of brimonidine from PLGA MPs (n=3). Also shown are the theoretical maximum and minimum amounts of brimonidine absorbed, based on 2 drops per day of 0.2% BT solution and 1-7% absorption (Ghate and Edelhauser, 2008) as well as 0.66 mg brimonidine per mg BT.

Having confirmed that the size and surface characteristics of the BTMPs were suitable for use in the rabbit model, the next step in the rational design process was to determine the 28-day release profile of drug from the MPs. Accordingly, in vitro release of BT from a known mass of these particles for over one month is represented in FIG. 2. As the goal was to release an amount of drug comparable to standard eye drop medication, the amount released as a concentration instead of percentage of total amount of drug encapsulated is reported. Also shown in FIG. 2 are the theoretical minimum and maximum amounts of topical BT 0.2% solution absorbed into the anterior chamber, as described in the methods section. As expected, the amount of BT released for the full month was within the upper and lower limits for absorption of topical BT 0.2%, with an average of 2.1±0.37 μg brimonidine/day released over 28 days. This average amount includes days 24-28, at which point release of brimonidine had slowed considerably.

3.2 Animal Studies

Figure 3:
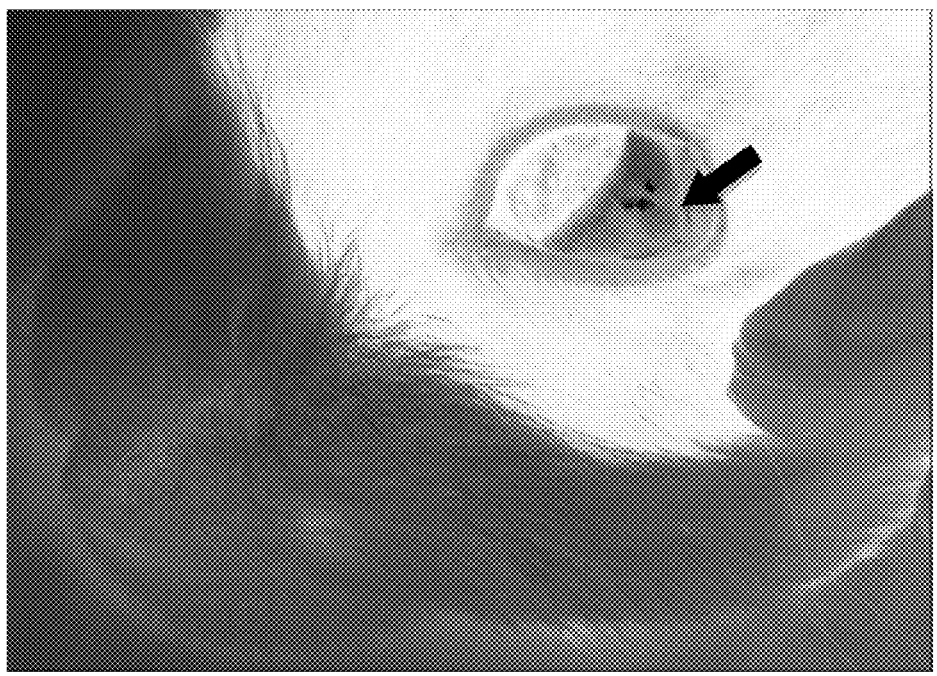
FIG. 3: BTMP bleb in subconjunctival space of Dutch belted rabbit on Day 1 of study.

Once the BTMP formulation was proven to release the drug locally according to design specifications, the ability of this released BT (in treated animals) to reduce IOP in a rabbit model over a 30-day time frame was tested. Approximately 5 mg in 0.05 ml of blank or drug-loaded MPs was injected into the superior subconjunctival space of pigmented Dutch belted rabbits on a 30 gauge needle (n=3 for each group initially; however, one rabbit in the blank MP group was removed from the study due to an adverse reaction to anesthesia unrelated to the MP injection or surgical manipulations). Blank MPs were used as the negative control as an indication of IOP in the absence of BT as well as the effect, if any of the PLGA microparticles on IOP and inflammation. FIG. 3 shows an example of the MP bleb in the subconjunctival space in one animal on Day 1 of the study. A third set of rabbits received twice-daily topical BT 0.2% drops at the same time each day to serve as the positive control.

The IOP was measured over 28 days by an ophthalmologist trained in pneumatonometry. For each measurement, the pneumatonometer result has a low standard deviation, generally <0.4 mm Hg. Initially, a baseline IOP measurement was taken on each rabbit before beginning treatment. Following administration of drug or MPs (blank or BT-loaded), IOP measurements were taken at the same time of day for each time point in the study, just before eye drops were administered to the positive control group. FIGS. 4a and 4b demonstrate the actual IOP values recorded at each time point for all three groups (blank MPs, topical BT drops, and BTMPs) in the right eye and left eye, respectively. IOP values are reported as the average IOP and standard deviation for the three animals in each group.

To better understand the changes in IOP over course of the study, the relative differences in IOP compared to each of the baseline values was calculated. FIGS. 5a and 5b depict the change in IOP at each time point compared to day 0 for all three groups, again in the right eye and left eye, respectively. IOPs recorded on Day 0 were not significantly different between animals in the blank MP, BTMP, and topical BT groups by one-way ANOVA. IOP reduction was significantly greater (p<0.05) in the BTMP group compared to the topical BT group for every time point in the right but not the left eye. While there was no sign of IOP reduction in the blank MP group, statistical analysis could not be performed for those animals after Day 0 due to the reduced sample size.

Figure 6:
FIG. 6: Partially degraded BTMPs in the subconjunctival space (stained with Masson's trichrome) following sacrifice on Day 28 of the study.

In addition to determining the efficacy of the BTMPs in vivo, the safety and compatibility of the PLGA MPs in the local environment throughout the 28-day study was investigated. Brimonidine was not detected in either the aqueous humor or plasma using an extremely sensitive HPLC method. Although this is expected for therapeutic levels (0.53-3.7 ug/day according to the calculations in Section 2.3), which implies that the amount released was below the detection limit of even HPLC, this does indeed suggest that higher, toxic levels of BT are not produced. As an additional measure of the safety of the BTMPs, the cornea, conjunctiva, anterior chamber, and periocular tissues were inspected using a portable slit lamp throughout the study for signs of inflammation. The only evidence of inflammation appeared to be related to surgical manipulations performed as part of the study, resulting in iridocorneal focal adhesions in the first week for all animals in the study. The location of these adhesions was consistent with iris plugging the 30 gauge needle paracentesis tracks that were used to collect aqueous samples. This inflammation was cleared prior to Day 14 of the study. Eyes were enucleated and stained using H&E, PAS, and Masson's trichrome for histological analysis following sacrifice of the rabbits on Day 28. The resulting slides revealed minimal amounts of fibrous tissue surrounding the area of injection (1-2 cell layers thick). No acute or chronic inflammation suggestive of a foreign body response or infection was present. Additionally, none of the histology evaluated showed any evidence of particle migration from the original injection site. The partially degraded MPs in the subconjunctival space can be seen in FIG. 6. Similar images for the remaining rabbits that received either blank or drug-loaded MPs showed that the tissue surrounding the MPs appeared normal.

Hydrogel/Microparticle Suspensions

The microparticles are added to the liquid hydrogel after it has been thoroughly washed and gently mixed to homogeneously suspend them. Incubation times of approximately 20-30 minutes are ideal for adequate suspension of particles. Typically we suspend 10-50 mg of particles in approximately 50 ul of gel solution.

The thermoresponsive gel developed for ocular delivery as described herein was tuned to have a phase transition temperature below 37° C. with sufficient crosslinking density to reversibly form an opaque gel. In this embodiment, the pNIPAAm-based gel transitions from a liquid to a gel over approximately 5 seconds at 34° C. In addition, the thermoreversible gels were designed to be non-degradable, as confirmed by dehydrating and weighing gel/microparticle samples in conjunction with the release study. Initial cytotoxicity testing of the gel/particle suspension on Chang conjunctival cell line (ATCC) showed no deleterious effects in vitro with a minimum of 5 washes, necessary to remove the initiating agents used during polymerization of the gel. The custom-designed BT release microparticles effectively provide release over one month as well when suspended in the gel as they do in free solution (see FIG. 8). In other words, the incorporation of the engineered microparticles into the gel does not significantly impact the intended release profile of BT from the system.

The microparticle/hydrogel suspensions can be administered to a rabbit to test whether the gelled member can remain in the lower fornix for a minimum of 30 days, whether or not the gelled member results in inflammation, and the ability of gelled member to reduce intraocular pressure in rabbits that have ocular hypertension (an experimental model of glaucoma). The microparticle/hydrogel suspensions also can be loaded with a gadolinium based contrast agent for magnetic resonance imaging to quantify the amount of contrast agent reaching different areas of the eye such as the cornea, retina, optic nerve, and systemic circulation. This will provide information about the usefulness of this system for delivering drugs for diseases other than glaucoma such as age-related macular degeneration and macular edema.

The effectiveness of the gelling eye drop formulation may be tested in a conventional, serial sacrifice-type study using a rabbit model of chronic glaucoma adapted from similar methods using non-human primates. New Zealand white rabbits may be used for this study because their eyes are similar in size to human eyes. To induce ocular hypertension, a 50 μl volume of 20 μm latex beads may be injected into the anterior chamber, which has been shown to result in increased IOP for up to 5 weeks, with a maximum of nearly twice the baseline IOP. To achieve increased IOP for the full study, we will inject the microbeads two times 5-6 weeks apart and IOP increase will be validated first in control animals. This model has also been shown to cause RGC axon death, making it a suitable model for determining the neuroprotective effect, if any, of our treatment method. Following confirmed induction of ocular hypertension, the rabbits will have one eye randomized to receive one of three therapies: BT solution 2 times a day (positive control), vehicle only delivery system of gel containing BT-free microparticles (negative control), and the BT-loaded microparticle/hydrogel drop. IOP will be measured using both pneumatonometry and rebound tonometry (using the TonoVet® handheld tonometer) several days before beginning treatment to establish a baseline. IOP measurements will be taken a minimum of three times per week from the onset of therapy until the end of the study, lasting up to three months. Aqueous samples will be drawn periodically from the anterior chamber on those days to measure levels of drug in the eye, and blood samples will be taken from the marginal ear vein to measure systemic concentrations of the drug. As systemic BT concentrations will likely be quite low, we will use established purification methods and high-performance liquid chromatography (HPLC) to perform these assays. The main outcome measures will be 1) reduction in IOP, 2) mean aqueous levels of drug, and 3) systemic concentration of the drug in blood samples. It is expected that the experimental delivery system tested in this study will demonstrate comparable (or better) IOP reduction and aqueous BT concentration when compared to the positive control group with a significantly lower systemic drug concentration. Slit lamp examination will also be used to evaluate for condition of the eyes prior to and during therapy to evaluate for any evidence of side effects.

Upon completion of the in vivo study, all eyes will be enucleated and prepared for histological analysis using paraffin embedding and staining techniques. The overall health and appearance of tissue surrounding the eye drop (cornea, sclera, conjunctiva, and eyelid) will be examined as well as other tissues of interest, particularly the retina and optic nerve to determine the in vivo toxicity after long-term exposure. More specifically, we will determine if any appreciable retinal ganglion cell (RGC) axon loss has occurred using common histopathological techniques. Any potential areas of damage will be identified using light microscopy and image analysis software (ImageJ, NIH) will be used to count the number of axons in each damage area for comparison between treated and control eyes.

The following groups and animal numbers, based on a power analysis of our preliminary in vivo IOP data, will be used to demonstrate statistically significant IOP reduction at each time point in our in vivo studies:

| Group description | Number of Rabbits |
|---|---|
| BT 0.15% drops twice daily | 5 |
| Gel and microparticles containing no drug | 5 |
| Gel and BT-loaded microparticles | 5 |
| Total per time point | 15 |

Although we have already seen success using both the microparticles and the hydrogel in vivo, it is possible that we will have issues with retention of the eye drop in some of the rabbits over one month. For instance, the presence of the nictitating membrane in rabbits may cause the drop to become dislodged over time, which, although not a concern for human patients, would affect the efficacy testing. In our initial work, we have been able to improve retention of the gel/microparticle drops by incorporating a mucoadhesive, water-soluble form of chitosan into the gel. Should retention still prove to be an issue at later time points (particularly in the three month formulation), a variety of minimally invasive options exist to mitigate this effect, including suturing of the gelled drop to the lower fornix, amputation of the nictitating membrane, or a one-time injection of botulinum toxin (such as Botox®, commonly used to treat strabismus in adults) to temporarily reduce functionality of the nictitating membrane. Another potential issue may be insufficient or inconsistent IOP increase in the rabbits receiving the microbead injection and a resultant lack of effect of treatment. Two types of tonometry will be used to ensure accurate measurements but if the initial validation of our in vivo glaucoma model does not show an adequate increase in IOP (defined as significantly higher IOP compared to baseline for at least 4 weeks), we will incorporate a third between the microbead injections at the beginning and midpoint of the study. In our experience and in independent studies of the microbead occlusion model in rodents, multiple injections have been shown to produce a consistent, longer duration of IOP increase. Thus we anticipate that using these techniques and a thorough initial validation would adequately address insufficiencies with our experimental model.

In Vivo Testing of Hydrogel/Microparticle Suspensions

Figure 11:
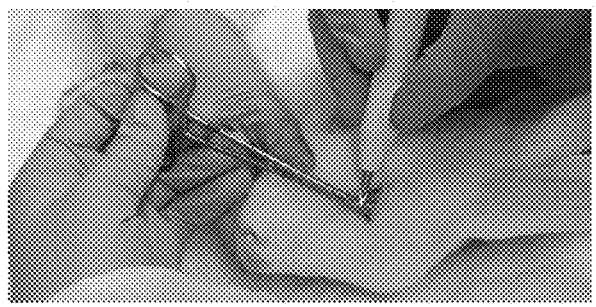
FIG. 11: A photo image of surgical resection of rabbit nictating membrane prior to drop administration.
Figure 12A:
FIGS. 12A and 12B: A photo image showing gel/microparticle drop administration (FIG. 12A). No restraint or sedation was used during this time for any of the rabbits. The presence of the gel drop in the inferior fornix was visually confirmed immediately following instillation (FIG. 12 B).
Figure 12B:
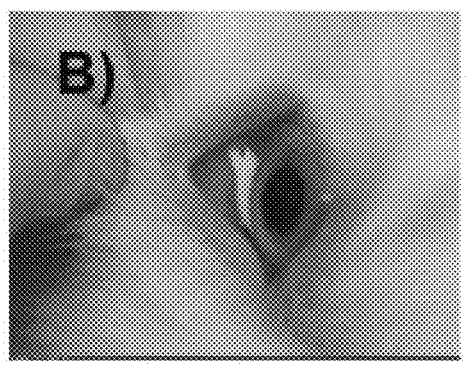
Figure 13:
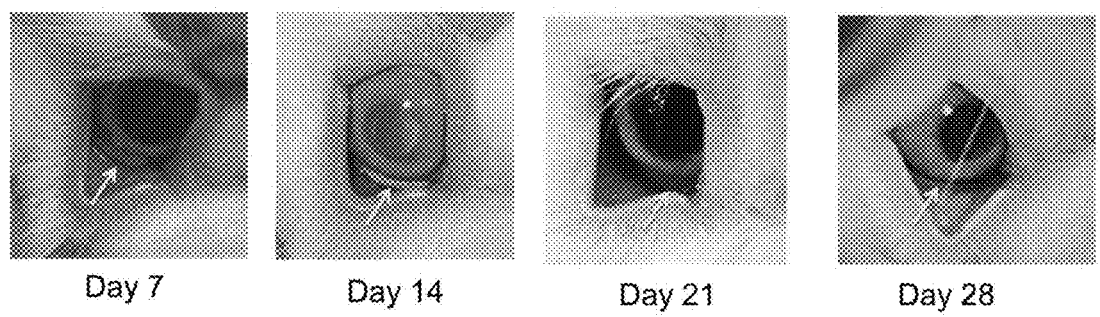
FIG. 13: Photo images showing the presence of gel/microparticle drop in inferior fornix from days 7-28. Note that visibility of the gels was greatly decreased from Day 21-28. Gels were stained with fluorescein to confirm presence.

The gel/microparticle drop was tested in a rabbit model over 28 days. The nictitating membrane (third eyelid) was resected prior to administering the drop in order to better represent retention in a human eye (see FIG. 11). The drop was administered with no prior restraint, sedation, or local anesthesia necessary (FIG. 12A). The findings were as follows:

The drops resulted in no irritation or infection in any of the rabbits, as evaluated using slit lamp examination. The drops were identified intact through 21 days, at which time the appearance of the gel/microparticle seemed to indicate that it had broken into smaller pieces (or that the drop had partially fallen out of or migrated away from the inferior fornix). FIG. 13 shows the gel/microparticle drops at various time points. The presence of the gels was confirmed using fluorescein staining and cobalt blue light, which differentiates the gel from surrounding tissues by giving it a bright green color.

Regardless of the appearance of the gels, the data suggest once again that intraocular pressure relative to the negative control group was significantly lower at every time points but one (presumably due to abnormally low pressure in the negative control group on that day, as seen in FIG. 14A). These results correspond well with those seen with both the microparticles alone and the positive control (topical eye-drop medication), with the exception that both experimental treatments actually outperformed the drops at the time of measurement on Day 14.

In the control eye, little to no effect on intraocular pressure was observed. This once again suggests that the experimental treatment had a markedly decreased systemic uptake compared to the traditional eyedrop medication group (FIG. 14B).

In Vitro Testing of Gd-DOTA Microparticles

We utilized the release behavior of BT (FIGS. 2 and 8) to generate design specifications and build the custom Gd-DOTA formulation. To confirm that the specifications for release behavior were met in the new Gd-DOTA formulation, we incubated a known mass of this formulation in a buffer solution and measured Gd-DOTA release over time using both MRI scans at predefined time points and also time-resolved fluorescence measurements (as a secondary method to confirm Gd-DOTA concentration). Although the data shown in FIG. 9 suggests that some minor formulation tuning may be required, the behavior of our preliminary Gd-DOTA formulation already corresponds extremely well with that of the BT release formulation, increasing the likelihood of successfully achieving our proposed aims. Similarly, these results further demonstrate the reliability of our in silico methods for preparing these type of release formulations. Overall loading of Gd-DOTA was also measured using inductively-coupled plasma mass spectrometry (ICP-MS) (and confirmed using the TRF spectrophotometric method) and determined to be 5.6 ug/mg microparticles. These loading results agree with those of Doiron et al. (2008) for 5 h release of Gd-DTPA, an alternative contrast agent with similar size and structure to Gd-DOTA, entrapped in PLGA microspheres.

To demonstrate the feasibility of quantifying local controlled release from a gel/microparticle depot using MRI, we performed post-mortem T1-weighted MRI scans of New Zealand White rabbits at 24 h following intravitreal injection (in the right eye only) of the Gd-DOTA loaded MP depot (FIG. 10a) and soluble Gd-DOTA (FIG. 10b), both contained within the thermoresponsive hydrogel matrix. Scans were performed within one hour of sacrifice. Soluble Gd-DOTA without MP encapsulation was largely cleared from the injection site at 24 h, with only 56% and 59% signal intensity (relative to nearby muscle tissue) in the vitreous and anterior chamber, respectively. In contrast, the controlled release Gd-DOTA loaded MPs generated a 690% and 347% larger signal intensity relative to that of muscle in the vitreous and anterior chamber, respectively (FIG. 10a). These results demonstrate our ability to track release and clearance of Gd-DOTA in the eye in whole brain scans as well as the slower release of Gd as indicated by the significant increase in signal intensity at 24 h in the Gd-DOTA loaded gel/MP depot. This placement allowed us to show that these agents could be located in whole animal scans and the corresponding release of Gd-DOTA can be quantified in various ocular tissues. We anticipate that, similar to our post-mortem results, the proposed in vivo studies will demonstrate a controlled release pattern from the gel/microparticle depot into the local environment analogous to the in vitro release data in FIG. 9. The spatiotemporal distribution of Gd-DOTA into the rest of the eye will also provide valuable data for future controlled release formulations of other ocular therapeutics, such as those targeting the posterior segment of the eye.

We will develop at least two Gd-DOTA-loaded microparticle formulations following a one-month release schedule (analogous to the current BT-loaded microparticle formulation) and also a three-month release schedule (analogous to the proposed BT-loaded microparticle formulation). Though the current Gd-DOTA microparticle formulation already shows good agreement for the former release schedule in vitro, we will make adjustments to pore size and particle size to diminish the initial burst seen in the first three days to achieve a better match to the one-month BT release. We will use MRI and spectrophotometry to detect the in vitro release of Gd-DOTA from the microparticles. Loading efficiencies will again be determined using TRF and confirmed with ICP-MS and the surface morphology and size of the particles will be determined in vitro prior to their use in vivo.

The candidate Gd-DOTA-loaded microparticles identified during in vitro testing will be tested in a healthy rabbit model, similarly to the BT-loaded, gelling eye drops. Administration of the gelling eye drops containing contrast agent will be done in the same way as with the drug-loaded version, in contrast to the preliminary studies in which MPs were injected intravitreally. We will scan the rabbits at various time points using high-resolution T1 mapping techniques in a 3T MRI scanner at the Neuroscience Imaging Center at the University of Pittsburgh throughout the study (lasting a maximum of three months) to determine the location and concentration of released contrast agent. The concentration of contrast agent in various ocular components, for example the anterior chamber and the vitreous, will be compared to BT concentration in those same tissues. Thus, we will be able to determine how well concentration of BT in various compartments of the eye follows concentration of contrast agent. The measure of success of these experiments will be release of Gd-DOTA to the local area of the gel/microparticle depot that matches concentration of BT in the same areas (as determined by aqueous samples taken from rabbits in the serial sacrifice study). Following completion of the in vivo MRI studies, we will once again perform slit lamp examination and tonometry measurements to evaluate the ocular health of the rabbits. We will also periodically take samples of aqueous humor and vitreous humor as well as venous blood samples from the marginal ear vein as a secondary confirmation of local and systemic contrast agent release. MRI and spectrophotometric Gd-DOTA concentration data will be compared to in vivo BT concentration data. Upon concluding the in vivo studies, eyes will be enucleated and evaluated for their overall appearance and health using common histopathological analysis techniques.

Three Month Release

This embodiment describes a formulation "recipe" that would be suitable for sustained, linear release of BT for a three-month period. More specifically, 90 days of linear release of BT may be realized using the following fabrication parameters: 1) Rp (overall particle radius)=10 μm, 2) Rocc (inner occlusion or pore size)=0.03 μm, 3) Mwd=256 kDa, 4) kCw (degradation rate constant)=1.00E-6 $days^{-1}$, and 5) a ratio of approximately 2% low MW, 27% middle MW, and 71% high MW poly(lactic-co-glycolic acid) (PLGA) containing 50% each of lactide and glycolide monomers. Microparticles will be fabricated using a standard double emulsion procedure from an organic solution of PLGA (a readily-translatable, biocompatible and biodegradable polymer) that is micro-emulsified along with an aqueous BT solution. The in vitro release of BT over three months will be tested by incubating a known mass of microparticles in a buffer solution at 37° C. Samples will be taken at regular intervals and buffer will be replaced to maintain sink-like conditions. The buffer samples containing BT will be assayed for BT concentration using spectrophotometric absorbance at a wavelength of 320 nm.

Modifying Phase Transition Properties of the Gel

Cross-linking density and concentration of other reagents play key roles in determining the phase transition time and temperature of the gel. The addition of poly(ethylene glycol) PEG (400 Da) enables the drop to be opaque (and therefore easily visible with the naked eye) and firm enough to be removed with tweezers. We can further tune the amount of PEG added and the molecular weight of PEG to lower the phase transition temperature closer to an ideal value of 27° C. (as low as possible while still being sufficiently above room temperature). The maximum loading of microparticles in drops will be determined by performing stability testing of the gelling drops in vitro. The gel/microparticle samples will be weighed at varying time points to ensure that, as with the original gel formulation, degradation of the drop is negligible over the timeframe of delivery.

Hydrogel/Microparticles with Other Drugs

The loading and release of other drugs (moxiflxacin and vancomycin) with the microparticles embedded within the gel has also been confirmed. This data indicates the use of this therapy for other ocular diseases (in this case, to treat ocular infection or for prophylactic use following ocular surgery).

In view of the many possible embodiments to which the principles of the disclosed invention may be applied, it should be recognized that the illustrated embodiments are only preferred examples of the invention and should not be taken as limiting the scope of the invention.

What is claimed is:

1. A liquid composition for ocular delivery of an agent to a subject, wherein said composition comprises agent-loaded polymer microparticles dispersed within a hydrogel comprising poly (n-isopropyl acrylamide), wherein the agent is an agent for treating an ocular condition, wherein said hydrogel comprises poly (ethylene glycol) and lacks polyethylene glycol diacrylate, wherein the composition is configured to form in situ a gelled, sustained release film structure having a thickness of 10 μm to 1000 μm retained on the lower fornix of an eye in the subject and is configured for sustained topical ocular release of the agent for a period of at least thirty days, and wherein the agent is travoprost, bimatoprost, latanoprost, unoprostine, methazolamide, timolol, levobunalol, carteolol, metipranolol, betaxolol, brimonidine, apraclonidine, pilocarpine, epinephrine, dipivefrin, carbachol, acetazolamide, dorzolamide, brinzolamide, or a pharmaceutically acceptable salt or ester thereof.

2. The composition of claim 1, wherein the liquid composition is in the form of an eye drop that can be self-administered by the subject.

3. The composition of claim 1, wherein the agent is an agent that lowers intraocular pressure, the microparticles are biodegradable, and the hydrogel is not biodegradable.

4. The composition of claim 1, wherein the agent-loaded polymer microparticles have a volume average diameter of 1 to 10 μm.

5. The composition of claim 1, wherein the polymer microparticles comprise poly glycolide, poly lactic acid, poly (lactic-co-glycolic acid), alginate, polycaprolactone, cellulose, dextran, chitosan, or a combination thereof.

6. The composition of claim 1, wherein the agent is encapsulated in the polymer microparticles.

7. The composition of claim 1, wherein the agent is brimonidine or a pharmaceutically acceptable salt or ester thereof.

8. The composition of claim 1, wherein the ocular condition is glaucoma, chronic dry eye, keratitis, post-operative inflammation, conjunctivitis, bacterial infection, or fungal infection.

9. The composition of claim 1, wherein the ocular condition is glaucoma.

10. The composition of claim 1, wherein the composition is configured to release the agent in an amount from 1 to 10 µg per day for a period of time of at least five days.

11. The composition of claim 1, wherein the sustained topical ocular release provides a rate of release that does not vary by more than 10% over a period of time of at least five days.

12. The composition of claim 1, wherein the sustained topical ocular release provides a rate of release that does not vary by more than 20% over a period of time of at least five days.

13. The composition of claim 1, wherein the agent manages elevated intraocular pressure in the eye.

14. The composition of claim 1, wherein the agent is brimonidine tartrate.

15. The composition of claim 1, wherein the agent-loaded polymer microparticles are suspended in the hydrogel.

16. The composition of claim 1, wherein the film structure has a thickness of 100 µm to 300 µm.

17. The composition of claim 1, wherein the film structure conforms to the shape of the lower fornix.

18. The composition of claim 1, wherein the film structure is opaque.

19. The composition of claim 1, wherein the film structure is passively retained on the lower fornix of the eye.

20. The composition of claim 1, wherein said hydrogel is opaque.

21. The composition of claim 1, wherein said hydrogel comprises chitosan.

* * * * *

UNITED STATES PATENT AND TRADEMARK OFFICE
CERTIFICATE OF CORRECTION

PATENT NO. : 12,396,959 B2
APPLICATION NO. : 17/580988
DATED : August 26, 2025
INVENTOR(S) : Morgan Virginia Fedorchak et al.

Page 1 of 1

It is certified that error appears in the above-identified patent and that said Letters Patent is hereby corrected as shown below:

In the Claims

Column 24, Line 36, Claim 1, please delete "poly (n-isopropyl acrylamide)" and insert therefor
-- poly(n-isopropyl acrylamide) --;

Column 24, Line 38, Claim 1, please delete "poly (ethylene glycol)" and insert therefor
-- poly(ethylene glycol) --;

Column 24, Line 45, Claim 1, please delete "unoprostine" and insert therefor -- unoprostone --; and Column 24, Line 46, Claim 1, please delete "levobunalol" and insert therefor -- levobunolol --.

Signed and Sealed this
Sixteenth Day of December, 2025

John A. Squires
*Director of the United States Patent and Trademark Office*